(12) United States Patent
Browne

(10) Patent No.: US 7,582,470 B2
(45) Date of Patent: Sep. 1, 2009

(54) DEVICE FOR AMPLIFYING AND DETECTING A TARGET NUCLEIC ACID

(75) Inventor: Kenneth A. Browne, Poway, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 10/621,803

(22) Filed: Jul. 17, 2003

(65) Prior Publication Data
US 2004/0023284 A1 Feb. 5, 2004

Related U.S. Application Data

(60) Provisional application No. 60/400,189, filed on Jul. 31, 2002.

(51) Int. Cl.
C12M 1/34 (2006.01)
C12M 3/00 (2006.01)
C07H 21/02 (2006.01)
C07H 21/04 (2006.01)
C12Q 1/68 (2006.01)
C12P 19/34 (2006.01)

(52) U.S. Cl. ............... 435/287.1; 435/6; 435/91.2; 435/287.2; 536/23.1; 536/24.3

(58) Field of Classification Search .............. 435/174, 435/283.1; 422/50, 68.1, 82.05
See application file for complete search history.

(56) References Cited

U.S. PATENT DOCUMENTS

| | | | |
|---|---|---|---|
| 5,118,801 A | 6/1992 | Lizardi et al. | |
| 5,312,728 A | 5/1994 | Lizardi et al. | |
| 5,639,612 A | 6/1997 | Mitsuhashi et al. | |
| 5,656,462 A | 8/1997 | Keller et al. | |
| 5,925,517 A | 7/1999 | Tyagi et al. | |
| 6,037,130 A | 3/2000 | Tyagi et al. | |
| 6,060,288 A | 5/2000 | Adams et al. | |
| 6,103,474 A | 8/2000 | Dellinger et al. | |
| 6,150,097 A | 11/2000 | Tyagi et al. | |
| 6,171,797 B1 | 1/2001 | Perbost | |
| 6,251,660 B1 | 6/2001 | Muir et al. | |
| 6,310,354 B1 * | 10/2001 | Hanninen et al. | 250/458.1 |

FOREIGN PATENT DOCUMENTS

WO WO 01/27327 A3 4/2001
WO WO 01/48242 A3 7/2001

OTHER PUBLICATIONS

Mueller, J. D. et al., "Self-sustained sequence replication (3SR): an alternative to PCR", Histochem. Cell Biol., vol. 108, pp. 431- 437 (1997).*
Stratagene Catalog, p. 39 (1988).*
Lund, V. et al., "Assessment of methods for covalent binding of nucleic acids to magnetic beads, Dynabeads TM, and the characteristics of the bound nucleic acids in hybridization reactions", Nucl. Acids Res., vol. 16, pp. 10861-10880 (1988).*
Gerard, G. F. et al., "Reverse Transcriptase. The use of Cloned Moloney Murine Leukemia Virus Reverse Transcriptase to Synthesize DNA from RNA" Mol. Biotech., vol. 8, pp. 61-77(1997).*
Ohyama, H. et al., Biotechniques, vol. 29, pp. 530-536 (2000).*
Wodicka, L. et al., Nature Biotechnol., vol. 15, pp. 1359-1367 (1997).*
Adessi at al., "Solid phase DNA amplification: characterisation of primer attachment and amplification mechanisms", Nucleic Acids Res., 2000, 28(20/e87):1-8, Oxford University Press, GB.
Alsina, at al., "Backbone Amide Linker (BAL) Strategy for N(alpha)-9-Fluorenylmethoxycarbonyl (Fmoc) Solid-Phase Synthesis of Unprotected Peptide p-Nitroanilides and Thioesters", J. Org. Chem., Nov. 26, 1999, 64(24):8761-9, American Chemical Society, US.
Arya et al., "Solid-Phase Synthesis of Oligomeric Deoxynucleic-Thiourea (DNT) and Deoxynucleic S-Methylthiourea (DNmt): a Neutral/Polycationic Analogue of DNA", Bioorganic & Med Chem Letters, 2000, 10:691-3, Elsevier Science Ltd., GB.
Brown et al., "Molecular beacons attached to glass beads fluoresce upon hybridisation to target DNA", Chem. Commun., 2000, 621-2, Royal Society of Chemistry, GB.
Canne et al., "A General Method for the Synthesis of Thioester Resin Linkers for Use in the Solid Phase Synthesis of Peptide-alpha-Thioacids", Tetrahedron Letters, 1995, 36(8):1217-20, Elsevier Science Ltd, GB.
Chan, et al., "The Biophysics of DNA Hybridization with Immobilized Oligonucleotide Probes", Biophys Journal, Dec. 1995, 69:2243-55, Biophysical Society, US.
Chu et al., "inhibition of DNA synthesis by cross-linking the template to platinum-thiol derivatives of complementary oligodeoxynucleotides", Nucleic Acids Res., 1989, 17(12):4783-98, Oxford University Press, GB.
Clippingdale et al., "Peptide Thioester Preparation by Fmoc Solid Phase Peptide Synthesis for Use in Native Chemical Ligation", J Peptide Sci., 2000, 6:225-34, European Peptide Society and John Wiley & Sons Ltd., GB.
Coleman et al., "Thionucleoside Disulfides as Covalent Constraints of DNA Conformation", Tetrahedron 1999, 55:12009-22, Elsevier Science Ltd., GB.
Fang et al., Designing a Novel Molecular Beacon for Surface-Immobilized DNA Hybridization Studies, J. Am. Chem. Soc., 1999, 121:2921-22, American Chemical Society, US.
Fang et al., "Molecular Beacons, Novel Fluorescent Probes", Analytical Chemistry, Dec. 1, 2000, 72:747A-53A. American Chemical Society, US.

(Continued)

Primary Examiner—Teresa E Strzelecka
(74) Attorney, Agent, or Firm—Michael J. Gilly

(57) ABSTRACT

Compositions, methods and devices for detecting nucleic acids. The invention particularly regards composite arrays of immobilized amplification primers and hybridization probes. Also disclosed are compositions and methods for covalently immobilizing oligonucleotides and other biological molecules to glass and plastic surfaces.

10 Claims, 7 Drawing Sheets

OTHER PUBLICATIONS

Fidanza et al., "Use of a Thiol Tether for the Site-Specific Attachment of Reporter Groups to DNA", J. Org. Chem., 1992, 57:2340-6. American Chemical Society, US.

Flouriot, et al., "Improved efficiency for primer extension by using a long, highly-labeled primer generated from immobilized single-stranded DNA templates", Nucleic Acids Res., 1997, 25(8):1658-9. Oxford University Press, GB.

Futaki et al, "Preparation of Peptide Thioesters using Fmoc-Solid Phase Peptide Synthesis and its Application to the Construction of a Template-Assembled Synthetic Protein (TASP)", Tetrahedron Letters, 1997, 38(35):6237-40. Elsevier Science Ltd., GB.

Goldstein et al., "An alternate preparation of thioester resin linkers for solid-phase synthesis of peptide C-terminal thioacids", Tetrahedron Letters, 2000, 41:2797-800. Elsevier Science Ltd., GB.

Hakala et al., "Detection of Oligonucleotide Hybridization on a Single Microparticle by Time-Resolved Fluorometry: Hybridization Assays on Polymer Particles Obtained by Direct Solid Phase Assembly of the Oligonucleotide Probes", Bioconjug. Chem., 1997, 8:378-84. American Chemical Society, US.

Hakala et al., "Time-Resolved Fluorescence Detection of Oligonucleotide Hybridization on a Single Microparticle: Covalent Immobilization of Oligonucleotides and Quantitation of a Model System", Bioconjug. Chem., 1997, 8:232-7. American Chemical Society, US.

Hatakeyama et al., "An Assay for Lectin Activity Using Microtiter Rate with Chemically Immobilized Carbohydrates", Analytical Biochem., 1996; 237:188-92. Academic Press, Inc., US.

Hatch et al., "Rolling circle amplification of DNA immobilized on solid surfaces and its application to multiplex mutation detection", Genetic Analysis: Biomolecular Engineering, 1999, 15:35-40. Elsevier Science, B.V., GB.

Hegner et al., "Immobilizing DNA on gold via thiol modification for atomic force microscopy imaging in buffer solutions", Federation of European Biochemical Societies Letters, 1993, 336(3):452-6. Elsevier Science Publishers, B.V., GB.

Hirayama, et al., "Improved immobilization of DNA to microwell plates for DNA-DNA hybridization", Nucleic Acids Res., 1996, 24(20):4098-9. Oxford Univeristy Press, GB.

Hoeg-Jensen et al., "Amino monothio acids in solid-phase synthesis of peptide thioamides", Int. J. Peptide Protein Res., 1996, 47:190-200. Munksgaard, GB.

Hovinen et al., "Novel Solid Supports for the Preparation of 3'-Derivatized Oligonucleotides: Introduction of 3'-Alkylphosphate Tether Groups Bearing Amino, Carboxy, Carboxamido, and Mercapto Functionalities", Tetrahedron, 1994, 50(24):7203-18. Elsevier Science Ltd., GB.

Hsieh et al., "Immobilization of invertase via carbohydrate moiety on chitosan to enhance its thermal stability", Biotech Letters, 2000, 22:1459-64. Kluwer Academic Publishers, Netherlands.

Ingenito et al., "Solid Phase Synthesis of Peptide C-Terminal Thioesters by Fmoc/t-Bu Chemistry", J. Am. Chem. Soc. 1999, 121:11369-74. American Chemical Society, US.

Ivanov et al., "Effect of Formaldehyde on the Efficiency of Hybridization of Dna Immobilized on Nitrocellulose Filters", 1992, Analytical Biochem., 206:414-8. Academic Press, Inc., US.

Kato et al., "Immobilization of DNA onto a Polymer Support and Its Potentiality as Immunoadsorbent", Biotech and Bioengineering, 1996, 51:581-90. John Wiley & Sons, Inc., US.

Kawai et al., "A Simple Method of Detecting Amplified DNA with Immobilized Probes on Microtiter Wells", Analytical Biochem., 1993, 209:63-9. Academic Press, Inc., US.

Kolodziej et al., "Stereoselective synthesis of 3-mercaptoproline derivates protected for solid phase peptide synthesis", Int. J. Peptide Protein Res., 1996, 48:274-80. Munksgaard, GB.

Kuijpers et al., "A New Strategy for the Solid-Phase Synthesis of 5'-Thiolated Oligodeoxynucleotides", Tetrahedron, 1993, 49(47):10931-44. Pergamon Press Ltd., GB.

Kumar et al., "The First Analogues of LNA (Locked Nucleic Acids): Phosphorothioate-LNA and 2'-Thio-LNA", Bioorganic & Med Chem Letters, 1998, 8:2219-22. Elsevier Science Ltd., GB.

Kumar et al., "Solid Phase Synthesis and Purification of 5'-Mercaptoalkylated Oligonucleotides", Bioorganica & Med. Chem. Letters, 1996, 6(6):683-8. Elsevier Science Ltd., GB.

Kumar et al., "Solid Phase Synthesis of Oligonucleotides Bearing Phosphate and Thiophosphate at Their 3'-Termini", Chemistry Letters, 1997, 1231-1232. The Chemical Society of Japan, JP.

Levesque, et al., "Reverse Transcription and PCR Amplification of Rare mRNAs Immobilized on Oligo(dT) Cellulose", Analytical Biochem, 1993, 213:170-1. Academic Press, Inc., US.

Li et al., "Direct preparation of peptide thioesters using an Fmoc solid-phase method", Tetrahedron Letters, 1998, 39:8669-72. Elsevier Science Ltd., GB.

Liang et al., "Polyvalent binding to carbohydrates immobilized on an insoluble resin", Biochemistry, Proc. Natl. Acad. Sci., 1997, 94:10554-9. National Academy of Sciences, US.

Lim et al., "A Luminescent Europium Complex for the Sensitive Detection of Proteins and Nucleic Acids immobilized on Membrane Supports", Analytical Blochem., 1997, 245:184-95. AB969961. Academic Press, US.

Liu et al., "A Fiber-Optic Evanescent Wave DNA Biosensor Based on Novel Molecular Beacons", Anal. Chem., 1999, 71:5054-9. American Chemical Society, US.

Liu et al., "Molecular Beacons for DNA Biosensors with Micrometer to Submicrometer Dimensions", Analytical Biochem., 2000, 283:56-63. Academic Press, US.

Manoharan et al., "A 2'-O-thiol tether in the ribose moiety of nucleic acids for conjugation chemistry", Gene, 1994, 149:147-56. Elsevier Science B.V., GB.

Marble et al., "RNA Transcription from Immobilized DNA Templates", Biotechnol. Prog., 1995, 11:393-6. American Chemical Society and American Institute of Chemical Engineers, US.

Mauro et al., "Fiber-Optic Fluorometric Sensing of Polymerase Chain Reaction-Amplified DNA Using an Immobilized DNA Capture Protein", Analytical Biochem., 1996, 235:61-72. Academic Press, Inc., US.

National Institute of Standards and Technology, "Characterization and Hybridization Reactions of Surface-Immobilized DNA", J. of Res. of the National Inst. Of Standards and Technology, Jan.-Feb. 1997, 102(1):110. National Institute of Standards & Technology, US.

National Institute of Standards and Technology, "Method Developed for Electrochemical Quatitation of Surface-Immobilized DNA", J. of Res. of the National Inst. of Standards and Technology, Mar.-Apr. 1998, 103(2):234. National Institute of Standards & Technology, US.

Nikiforov et al., "The Use of 96-Well Polystyrene Plates for DNA Hybridization-Based Assays: An Evaluation of Different Approaches to Oligonucleotide Immobilization", Analytical Biochem., 1995, 227:201-9. Academic Press, Inc., US.

Okahata et al., "Kinetic Studies of Sequence-Specific Binding of GCN4-bZIP Peptides to DNA Strands Immobilized on a 27-MHz Quartz-Crystal Microbalance", Biochemistry, 1998, 37:5666-72. American Chemical Society, US.

Okamoto et al., "Microarray fabrication with covalent attachment of DNA using Bubble Jet technology", Nature Biotechnology, 2000, 18:438-41. Nature Publications Group, Macmillan Pub. Ltd., GB.

Peterlinz et al., "Observation of Hybridization and Dehybridization of Thiol-Tethered DNA USing Two-Color Survace Plasmon Resonance Spectroscopy", J. Am. Chem. Soc., 1997, 119:3401-2. American Chemical Society, US.

Peterson et al., "Kinetic Control of Hybridization in Surface Immobilized DNA Monolayer Films", J. Am. Chem. Soc., 2000, 122:7837-8. American Chemical Society, US.

Pirrung et al., "Novel Reagents and Procedures for Immobilization of DNA on Glass Microchips for Primer Extension", Langmuir, 2000, 16:2185-91. American Chemical Society, US.

Pividori et al, "Electrochemical genosensor design: immobilization of oligonucleotides onto transducer surfaces and detection methods", Biosensors & Bioelectronics, 2000, 15:291-303. Elsevier Science S.A., GB.

Rajagopalan et al., "A Simple Procedure for the Preparation of 4-(alpha-Mercaptobenzyl)Phenoxyacetic Acid, a Thiol Linker Unit Used in Solid Phase Synthesis of Peptide-alpha-Thioacids", Synthetic Communications, 1997, 27(1):187-94. Marcel Dekker, Inc., US.

Rasmussen et al., "Covalent Immobilization of DNA onto Polystyrene Microwells: The Molecules Are Only Bound at the 5' End", Analytical Biochem., 1991, 198:138-42. Academic Press, Inc., US.

Riccelli et al., "Hybridization of single-stranded DNA targets to immobilized complementary DNA probes: comparison of hairpin versus linear capture probes", Nucleic Acids Res., 2001, 29(4):996-1004. Oxford University Press, GB.

Rogers et al., "Immobilization of Oligonucleotides onto a Glass Support via Disulfide Bonds: A Method for Preparation of DNA Microarrays", Analytical Biochem., 1999, 266:23-30. Academic Press, US.

Satoh et el., "Comparison of Methods of Immobilization to Enzyme-Linked Immunosorbent Assay Plates for the Detection of Sugar Chains", Analytical Biochem., 1999, 275:231-5. Academic Press, US.

Skryabin et al., "A crude lysate of cells immobilized on solid support can serve as a matrix for enzymatic DNA amplification", Nucleic Acids Res., 1990, 18(14):4289. Oxford University Press, GB.

Steel et al., "Immobilization of Nucleic Acids at Solid Surfaces: Effect of Oligonucleotide Length on Layer Assembly", Biophysical Journal, 2000, 79:975-81. Biophysical Society, US.

Steemers et al., "Screening unlabeled DNA targets with randomly ordered fiber-optic gene arrays", Jan. Nature Biotechnology, 2000, 18: 91-4. Nature Publications Group, Macmillan Pub. Ltd., GB.

Strother et al., "Covalent attachment of oligodeoxyribonucleotides to amine-modified Si(001) surfaces" Nucleic Acids Res., 2000, 28(18):3535-41. Oxford University Press, GB.

Tang et al., "Matrix-assisted laser desorption/ionization mass spectrometry of immobilized duplex DNA probes", Nucleic Acids Res., 1995, 23(16):3126-31. Oxford University Press, GB.

Walsh et al., "Optimizing the Immobilization of single-stranded DNA onto glass beads", J. Biochem. Biophys. Methods, 2001, 47:221-31. Elsevier Science, B.V., GB.

Weber et al., "Preparation of surface modified protein nanoparticles by introduction of sulfhydryl groups", International Journal of Pharmaceutics, 2000, 211:67-78. Elsevier Science, B.V., GB.

Whitcombe et al., "Detection of PCR products using self-probing amplicons and fluorescence", Nature Biotechnology, 1999, 17:804-7. Nature Publications Group, Macmillan Pub. Ltd., GB.

Winger et al., "A Convenient Route to Thiol Terminated Peptides for Conjugation and Surface Functionalization Strategies", Bioconjug Chem., 1995, 6:323-6. American Chemical Society, US.

Yang et al., "Adsorption Kinetics and Ligand-Binding Properties of Thiol-Modified Double-Stranded DNA on a Gold Surface", Langmuir, 1998, 14:6121-9. American Chemical Society, US.

Yang. et al., "Covalent Immobilization of Oligonucleotides on Modified Glass/Silicon Surfaces for Solid-phase DNA Hybridization and Amplification", Chemistry Letters, 1998, 257-8. The Chemical Society of Japan, JP.

Yang et al., "Fast Hybridization Solution for the Detection of Immobilized Nucleic Acids", Product Application Focus, BioTechniques, 1995, 18(3):498-503. Eaton Publishing, US.

Yoo et al., "Synthesis of Oligonucleotides Containing 3'-Alkyl Carboxylic Acids Using Universal, Photolabile Solid Phase Synthesis Supports", J. Org. Chem., 1995, 60:3358-64. American Chemical Society, US.

Zhao et al., "DNA-modified electrodes; part 4: optimization of covalent immobilization of DNA on self-assembled monolayers", Talanta, 1999, 49:751-6. Elsevier Science B.V., GB.

Majlessi et al., "Advantages of 2'-O-methyl oligoribonucleotide probes for detecting RNA targets," Nucl. Acid Res., 1998, 26(9):2224-2229, Oxford University Press, USA.

* cited by examiner

SEQUENCE LISTING

```
<160> NUMBER OF SEQ ID NOS: 7
<210> SEQ ID NO 1
<211> LENGTH: 20
<212> TYPE: DNA
<213> ORGANISM: Human

<400> SEQUENCE: 1
gatatacgtg ccaggtggag                                              20

<210> SEQ ID NO 2
<211> LENGTH: 8
```

```
<212> TYPE: PRT
<213> ORGANISM: Human

<400> SEQUENCE: 2

Asp Arg Val Tyr Ile His Pro Phe
 1               5

<210> SEQ ID NO 3
<211> LENGTH: 50
<212> TYPE: DNA
<213> ORGANISM: Artificial Sequence
<220> FEATURE:
<223> OTHER INFORMATION: HIV-1 specific T7 promoter-primer

<400> SEQUENCE: 3
aatttaatac gactcactat agggagagtt tgtatgtctg ttgctattat          50

<210> SEQ ID NO 4
<211> LENGTH: 19
<212> TYPE: DNA
<213> ORGANISM: HIV-1

<400> SEQUENCE: 4
acagcagtac aaatggcag                                            19

<210> SEQ ID NO 5
<211> LENGTH: 22
<212> TYPE: RNA
<213> ORGANISM: Artificial Sequence
<220> FEATURE:
<223> OTHER INFORMATION: HIV-1 specific molecular beacon
<220> FEATURE:
<221> NAME/KEY: misc_feature
<222> LOCATION: (1)...(22)
<223> OTHER INFORMATION: 2'-methoxy nucleotides

<400> SEQUENCE: 5
gcgaguacag ugcagggcuc gc                                        22

<210> SEQ ID NO 6
<211> LENGTH: 23
<212> TYPE: RNA
<213> ORGANISM: Artificial Sequence
<220> FEATURE:
<223> OTHER INFORMATION: HIV-1 specific molecular beacon
<220> FEATURE:
<221> NAME/KEY: misc_feature
<222> LOCATION: (1)...(23)
<223> OTHER INFORMATION: 2'-methoxy nucleotide analogs

<400> SEQUENCE: 6
gcgaguacag ugcaggggcu cgc                                       23

<210> SEQ ID NO 7
<211> LENGTH: 24
<212> TYPE: RNA
<213> ORGANISM: Artificial Sequence
<220> FEATURE:
<223> OTHER INFORMATION: HIV-1 specific molecular beacon
<220> FEATURE:
<221> NAME/KEY: misc_feature
<222> LOCATION: (1)...(24)
<223> OTHER INFORMATION: 2'-methoxy nuucleotides

<400> SEQUENCE: 7
ccgaggguac agugcagggc ucgg                                      24
```

DEVICE FOR AMPLIFYING AND DETECTING A TARGET NUCLEIC ACID

RELATED APPLICATIONS

This application claims the benefit of U.S. Provisional Application No. 60/400,189, filed Jul. 31, 2002. The entire disclosure of this related application is hereby incorporated by reference.

FIELD OF THE INVENTION

The present invention relates to the field of nucleic acid chemistry. More specifically, the invention relates to methods of making and using devices that incorporate immobilized oligonucleotides.

BACKGROUND OF THE INVENTION

The molecular diagnostics industry has been revolutionized by the advent of nucleic acid amplification technology. Enzyme-based nucleic acid amplification is conventionally practiced using at least two oligonucleotide primers, each primer being complementary to an opposite strand of the nucleic acid that is to be amplified. Also conventionally, the primers are soluble and able to diffuse freely through solution to encounter a complementary target. Upon binding the target, a polymerase enzyme extends the primers using the target nucleic acid sequence as a template for the synthesis of new strands. Detection of the newly synthesized strands provides, either directly or indirectly, a means for detecting the target nucleic acid. As the field has evolved, there has been an emphasis on the development of methods that, in addition to being highly sensitive, are reliable, amenable to automated formats, and minimize the opportunity for operator error.

Various approaches have been used to simplify the manipulations needed to prepare amplification reactions and then carry out amplicon detection steps. For example, reagents used in the amplification step have been freeze-dried so that reconstitution with buffer and addition of a target sample is all that is required to prepare a complete solution-based reaction (see U.S. Pat. No. 5,834,254). In a different approach, self-reporting probes were used in solution-based amplification procedures to avoid the need for separate addition of probe reagents (see U.S. Pat. No. 6,037,130). In yet another instance, electronic biasing was used to direct biotin-labeled amplification primers to discrete areas on a streptavidin-coated microelectronic chip. After immobilizing at those locations, the anchored primers were extended in place by the action of a polymerase using a complementary target sequence as a template, with the extension product being detected following heat denaturation and hybridization of a reporter probe (Westin et al., *Nature Biotechnology* 18: 199 (2000)). Unfortunately, a stoichiometric relationship between the number of arrayed primers immobilized on the chip and the number of extension products available for detection limits the sensitivity of this latter, microarray-based technique.

The art field generally accepts that microarrays are one of the most promising technologies of the post-genomic era. Simply stated, a microarray is a solid substrate that has molecules immobilized, typically as a grid on its surface. Over 95% of microarray work performed today is carried out using DNA—either cDNA or oligonucleotides—in hybridization formats similar to Southern blotting. While protein microarrays represent an emerging technology, their development has been hampered somewhat because the active conformations of complex proteins have been difficult to preserve through the necessary immobilization procedures. (*Gen. Eng. News* 21:9 (2001))

The introduction of arraying devices based on inkjet or contact printing technology has greatly simplified laboratory-scale production of microarrays. Indeed, arraying devices for depositing picoliter droplets of solutions onto glass or plastic substrates to create microarrays are now widely available. Rather than synthesizing an oligonucleotide directly on the microarray substrate, these devices allow pre-formed oligonucleotides, or other biological molecules, to be dispensed onto the substrate in a quantity and pattern specified by the user.

One of the challenges underlying efficient production of microarrays relates to the immobilization chemistry that joins the deposited macromolecules to the solid substrate. As indicated above, oligonucleotides have been biotinylated, deposited onto streptavidin-coated surfaces, and immobilized by the noncovalent streptavidin:biotin interaction. While convenient, this approach may not be cost-effective for industrial-scale production. Other approaches based on covalent immobilization chemistries are frequently burdened by complicated synthetic routines that lead to inefficiencies in the yield of desired products.

The present invention addresses the need for nucleic acid amplification techniques that are specific and highly sensitive, and that are compatible with disposable format assays requiring minimal reagent preparation and operator involvement for detection of nucleic acid targets. Also provided is a convenient and versatile covalent immobilization chemistry that may be used for attaching macromolecules to glass and plastic surfaces.

SUMMARY OF THE INVENTION

A first aspect of the invention relates to a device for amplifying and detecting a target nucleic acid. The invented device includes: (a) a solid support having a surface, (b) at least one species of oligonucleotide immobilized substantially uniformly over the surface of the solid support, thereby defining a field of immobilized oligonucleotides, wherein the oligonucleotide is complementary to a first strand of the target nucleic acid, and (c) a plurality of hybridization probes immobilized to the solid support at discrete positions within the field of immobilized oligonucleotides. In a preferred embodiment, the surface of the solid support is made of either glass or plastic. When this is the case, the at least one species of oligonucleotide immobilized uniformly over the surface can be immobilized covalently. Alternatively, and regardless of whether the solid support is made of glass or plastic, the plurality of hybridization probes immobilized to the solid support can be immobilized covalently. In another embodiment, and again regardless of whether the solid support is made of glass or plastic, the at least one species of oligonucleotide and the plurality of hybridization probes are both immobilized covalently. More preferably, the device further includes at least one soluble oligonucleotide that is complementary to an opposite strand of the target nucleic acid, in which case the first strand and the opposite strand of the target nucleic acid are complementary to each other. In still another embodiment, the plurality of hybridization probes includes a plurality of self-reporting probes. More preferably, each of the plurality of self-reporting probes includes a fluorophore moiety. In a highly preferred embodiment of the invented device, the at least one species of oligonucleotide immobilized uniformly over the surface of the solid support includes a promoter sequence for an RNA polymerase.

A second embodiment of the invention relates to a method of making a device for amplifying and detecting a target nucleic acid. The invented method includes the steps of: (a) obtaining a solid support having a surface; (b) immobilizing to the surface at discrete positions thereon at least two different hybridization probes to produce a probe array; and (c) contacting the probe array with a composition that includes an oligonucleotide complementary to a first strand of the target nucleic acid, whereby the oligonucleotide immobilizes to the surface substantially uniformly. In one embodiment, the immobilizing step involves spotting with a mechanical arrayer. When this is the case, the contacting step may involve dispensing with a mechanical pipettor a liquid volume of the composition which is sufficient to immerse said probe array. In another embodiment, the surface of the solid support is made of glass or plastic. In a preferred embodiment, the solid support may include a multiwell plate, and the surface may be the planar inner surface of a single well contained in the multiwell plate. In another preferred embodiment, the hybridization probes and the oligonucleotide primer are each immobilized to the surface by covalent bonds. For example, the covalent bond can be an amide bond. Alternatively, when the hybridization probes and the oligonucleotide primer are each immobilized to the surface by covalent bonds, the hybridization probes may include a fluorophore moiety and a quencher moiety. In a highly preferred embodiment, the hybridization probes are molecular beacons.

A third aspect of the invention relates to a kit for detecting a target nucleic acid. This kit typically will contain: (1) one of the above-described devices; (2) a soluble oligonucleotide primer; and (3) a positive-control nucleic acid which is amplifiable in a nucleic acid amplification reaction using the at least one species of oligonucleotide primer immobilized uniformly over said surface in combination with the soluble oligonucleotide primer.

A fourth aspect of the invention relates to a method of detecting a target nucleic acid. This method involves first obtaining one of the above-described devices, and thereafter contacting the field of immobilized oligonucleotide primers and the plurality of different hybridization probes of the device with a sample containing: the target, a soluble oligonucleotide primer, and at least one enzyme having a DNA polymerase activity under amplification promoting conditions for a time sufficient to allow synthesis of amplicons. Next, there is a step for detecting a signal indicative of hybrid duplex formation from at least one of the plurality of different hybridization probes. Detection of the signal will indicate detection of the target nucleic acid.

A fifth aspect of the invention relates to a method of chemically bonding a biomolecule to a solid support. The invented method involves first providing a solid support that includes a plurality of nucleophilic moieties. These nucleophilic moieties may be either hydroxyl moieties or sulfhydryl moieties. Next, there is a step for providing a carboxylated biomolecule. Finally, there is a step for contacting the carboxylated biomolecule and the solid support under reaction conditions sufficient to promote bonding between the solid support and the biomolecule. In a preferred embodiment, the contacting step involves contacting the biomolecule and the solid support in the presence of EDAC. In a more preferred embodiment, the solid support includes a glass surface. In a more highly preferred embodiment, the plurality of nucleophilic moieties included on the glass surface are a plurality of sulfhydryl moieties. When this is the case, the reaction-promoting conditions can include aqueous conditions buffered to a pH of from 5-9. In accordance with another preferred embodiment, when the plurality of nucleophilic moieties included on the glass surface is a plurality of sulfhydryl moieties, the reaction-promoting conditions can include an EDAC concentration of between 50 and 200 mM. In a different preferred embodiment, the carboxylated biomolecule further includes a fluorophore moiety. In general, the carboxylated biomolecule can be either a carboxylated oligonucleotide, a carboxylated carbohydrate, a carboxylated peptide or a carboxylated protein. In a particular embodiment, the carboxylated biomolecule is a carboxylated oligonucleotide. In a highly preferred embodiment, the carboxylated oligonucleotide includes a fluorophore moiety, and in an even more highly preferred embodiment the carboxylated oligonucleotide that includes a fluorophore moiety further includes a quencher moiety.

Definitions

As used herein, an "oligonucleotide" is a polymeric chain of at least two, generally between about five and about 100, chemical subunits, each subunit comprising a nucleotide base moiety, a sugar moiety, and a linking moiety, such as a phosphate group, that joins the subunits in a linear spatial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may contain chemical analogs of nucleotide bases, sugars, and backbone-linking moieties. The term particularly includes analogs, for example having a methoxy group at the 2' position of the ribose (OMe), as well as synthetic linkers that include, for example, a carboxylate moiety. Oligonucleotides may be purified from naturally occurring sources, but preferably are synthesized using any of a variety of well known enzymatic or chemical methods and may contain nucleotide analogs.

As used herein, "polynucleotide" means either RNA or DNA, along with any nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. A label may be joined, directly or indirectly, to an oligonucleotide or other biological molecule. Direct labeling can occur through bonds or interactions that link the label to the probe, including covalent bonds or non-covalent interactions such as hydrogen bonding, hydrophobic and ionic interactions, or through formation of chelates or coordination complexes. Indirect labeling can occur through use of a bridging moiety or "linker", such as an antibody or additional oligonucleotide(s), which is/are either directly or indirectly labeled. Labels can be any known detectable moiety, such as, for example, radionuclides, a ligand (e.g., biotin, avidin), or a chromophore, such as a dye or particle that imparts a detectable color (e.g., latex beads or metal particles), luminescent compounds (e.g., bioluminescent, phosphorescent or chemiluminescent labels) and fluorescent compounds.

As used herein, a "solid support" is any material that maintains its shape under assay conditions, and that can be separated from a liquid phase. Examples of preferred solid supports include materials made from glass or plastic.

As used herein, "microparticles" are solid or semi-solid particles having a diameter of less than one millimeter, more preferably less than 100 microns, still more preferably less than 10 microns, which can be formed of a variety of materials, including glass or plastic, as well as derivatized glass or plastic. Preferred microparticles are monodisperse (i.e., uniform in size within about 5%), thereby providing consistent results which are particularly advantageous for use in an automated assay.

As used herein, "reaction conditions sufficient to promote bonding" refers to the aggregated conditions of time, temperature, and chemical environment (including factors such as solvent, pH, and reactant concentrations), that permit physical interaction and allow covalent bond formation between two chemical species.

As used herein, "amplification" or "nucleic acid amplification" or "polynucleotide amplification" refers to an in vitro procedure for obtaining multiple copies of a target nucleic acid sequence, its complement or fragments thereof.

An "amplicon" is a polynucleotide product generated in an amplification reaction.

An "analyte amplicon" is a polynucleotide product of an amplification reaction wherein an analyte polynucleotide served as the template for synthesis of polynucleotide copies or amplification products.

By "target" is meant a specific deoxyribonucleotide or ribonucleotide molecule containing a target nucleobase sequence which may be hybridized by a probe or amplification primer. Exemplary targets include viral polynucleotides, bacterial polynucleotides (such as rRNA), and eucaryotic mRNA. In the context of nucleic acid amplification reactions, a target polynucleotide includes a target sequence to be replicated, may be either single-stranded or double-stranded, and may include sequences in addition to the target sequence, which additional sequences may not be amplified.

A "target sequence" refers to the particular nucleotide sequence of the target polynucleotide which may be hybridized by a complementary detection probe or amplification primer.

By "transcription associated amplification" is meant nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a reverse transcriptase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al., are preferred for conducting nucleic acid amplification procedures of the type disclosed herein.

As used herein, an "array" is an orderly spatial arrangement of samples. A nucleic acid array provides a medium for matching known and unknown nucleic acid samples based on base-pairing rules, and for automating the process of identifying and/or quantifying unknowns. Although arrays that are useful in connection with the invention may have any number of spatially separated samples or "spots" contained therein, certain preferred arrays have 1-100 spots, more preferably 1-81 spots, more preferably 1-64 spots, more preferably 1-49 spots, more preferably 1-36 spots, more preferably 1-25 spots, more preferably 1-16 spots, more preferably 1-9 spots, and still more preferably 1-4 spots.

As used herein, a "molecular beacon" or "molecular beacon probe" is an oligonucleotide probe having a stem-and-loop structure that hybridizes specifically to a target polynucleotide under conditions that promote hybridization to form a detectable hybrid. Molecular beacons have been described in U.S. Pat. No. 6,103,476.

With reference to amplification primers, hybridization probes, or other compounds, "immobilized" is meant to convey that the compound joins, directly or indirectly, to a solid support. Immobilized compounds may be joined to the solid support by covalent or non-covalent interactions.

As used herein, a "probe" is an oligonucleotide that hybridizes specifically to a target sequence in a nucleic acid, preferably in an amplified nucleic acid, under conditions that promote hybridization, to form a detectable hybrid. A probe may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A probe may comprise target-specific sequences and other sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "amplification primer" is an oligonucleotide that hybridizes to a target nucleic acid, or its complement, and participates in a nucleic acid amplification reaction. Amplification primers, or more simply "primers," may be optionally modified oligonucleotides which are capable of hybridizing to template nucleic acids and which have 3'-ends that can be extended by a DNA polymerase activity.

As used herein, two molecules, such as an amplification primer and a hybridization detection probe, are said to be in "fluid communication" with each other when a third species, such as an amplicon, is able to freely interact with either or both of the two molecules. Two molecules that are in fluid communication with each other may, for example, be in the same well of a microplate with no physical barrier between the molecules.

BRIEF DESCRIPTION OF THE DRAWINGS

FIG. 1A illustrates a silanization reaction that introduces sulfhydryl functional groups onto a glass surface. FIG. 1B shows how a carboxylated oligonucleotide may react with EDAC to activate the oligonucleotide for reaction with a strong nucleophile. FIG. 1C shows how a nucleophilic sulfhydryl can react with an EDAC-activated oligonucleotide to result in a covalently immobilized oligonucleotide.

FIG. 2A shows results for different solvent compositions. FIG. 2B shows results for different silane concentrations.

FIG. 3A illustrates results for reactions conducted using an amine-derivatized surface. FIGS. 3B and 3C illustrate results for reactions conducted using a sulfhydryl-derivatized surface.

FIG. 4A shows results for a collection of solution TMA reactions conducted using 100 copies of nucleic acid target. FIG. 4B shows results for a collection of TMA reactions conducted using an immobilized primer and 100,000 copies of the nucleic acid target.

FIG. 5A shows results for arrayed spots of molecular beacon L following a TMA reaction using only soluble primers and 100,000 copies of the target nucleic acid, while FIG. 5B shows similar results obtained using molecular beacon SL. FIG. 5C shows results for arrayed spots of molecular beacon L following a TMA reaction using one soluble primer, one immobilized primer and 100,000 copies of the target nucleic acid, while FIG. 5D shows similar results obtained using molecular beacon SL.

DETAILED DESCRIPTION OF THE INVENTION

Figure 1A:
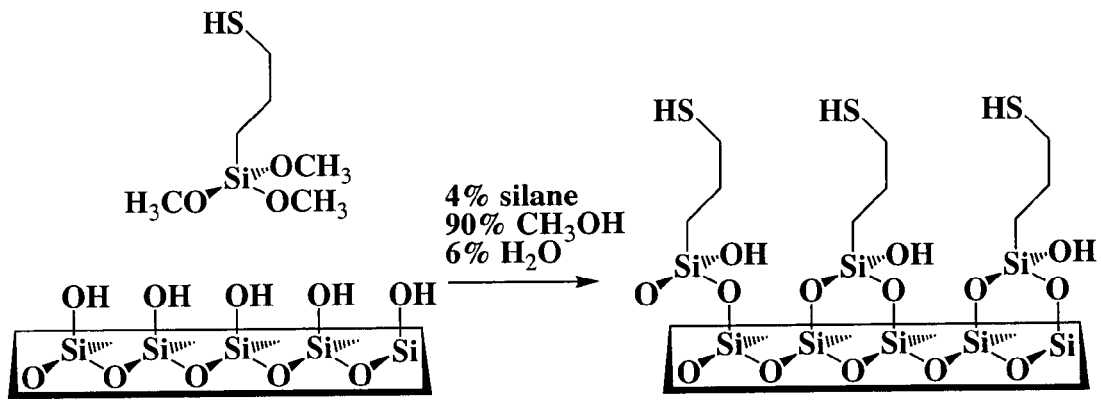
FIGS. 1A-1C show chemical structures that are relevant to oligonucleotide immobilization.

Herein there are disclosed methods of making and using devices for conducting nucleic acid amplification reactions. The invention particularly embraces methods of manufacturing which optionally may employ, but are not limited to, the immobilization chemistries described below. In accordance with certain embodiments, a nucleic acid amplification reaction is conducted in contact with a solid support having disposed thereon at least one species of immobilized amplification primer. In a preferred embodiment, the immobilized amplification primer is one member of a pair of oppositely disposed oligonucleotides, one each being complementary to opposite strands of the target nucleic acid that is to be amplified. The primers are oriented such that the extension product of a first primer can serve as the template for hybridization and extension of the opposite strand primer. In another embodiment, there is immobilized to the same solid support at least one probe for detecting amplicons generated using the immobilized amplification primers. In highly preferred embodiments, the probe is a self-reporting probe such a molecular torch or molecular beacon. Manufacturing of the device advantageously eliminates the need for maintaining spatial separation between the immobilized probes and primers, and so greatly simplifies unit construction.

The invention further regards methods for covalently joining pre-formed macromolecules to glass and plastic surfaces. Other surfaces, including mica and gold surfaces, are particularly contemplated for use in connection with the present invention. Although the described immobilization chemistry may be used for attaching peptides, proteins or carbohydrates to surfaces, the most highly preferred embodiments of the invention involve the immobilization of oligonucleotides. The oligonucleotides or other biomolecules may be attached to surfaces in discrete spots on planar surfaces that characterize microarrays, or over dispersed areas on particulates or planar surfaces. Immobilization of labeled oligonucleotides by the invented method advantageously gave high levels of specific coupling that were indicated by high signal-to-noise ratios (S/N). Thus, oligonucleotides can be immobilized with very high efficiency using the methods described herein.

Devices for Amplifying Nucleic Acids—Composite Arrays

Particularly preferred devices for amplifying nucleic acids are referred to herein as "composite arrays." These devices include a plurality of hybridization detection probes spatially arranged or arrayed at discrete locations on a solid support. The different immobilized probes of the composite array are separated from each other, but are interspersed among an otherwise uniformly distributed collection of immobilized amplification primers. The resulting device can be used for carrying out both amplification and detection of target nucleic acids in a convenient format. Advantageously, immobilization of primers reduces the opportunity for undesirable primer dimer formation during an amplification reaction, and the arrangement of the primers in this fashion maximizes the amount of primers that can be immobilized and simplifies the manufacturing process.

Composite arrays conventionally include at least two different probe species, and at least one immobilized amplification primer species. For example, the immobilized probes may be specific for an amplicon corresponding to a target of interest, and to a positive control amplicon. The probe species can be disposed as individual spots, each spatially separated from the other, in an array or microarray format. The immobilized primer of the composite array has a free 3' terminus available for extension by a DNA polymerase activity when the primer is hybridized to a complementary target nucleic acid. Primers may be immobilized by their 5' ends, or by linkers disposed within the sequence of the primer as long as the linkers do not substantially inhibit the formation of a duplex between the primer and its complementary target nucleic acid or polymerase activity. In a preferred embodiment, the immobilized primer is complementary to only one of the strands of the nucleic acid that is to be amplified. According to this embodiment, an opposite strand primer which is soluble may be used in conjunction with the immobilized primer to carry out a nucleic acid amplification reaction.

The structure of an exemplary composite array is illustrated more particularly by the following example. A composite array for detecting HIV nucleic acids has two spots immobilized on the inner bottom surface of a well of a plastic multiwell plate, each spot being separated from the other and each containing a different hybridization probe. The first spot contains a molecular beacon having binding specificity for an HIV amplicon. The second probe has specificity for a different amplicon which serves as a positive control in an amplification reaction conducted in the well containing the composite array. Also immobilized on the inner bottom surface of the well is an amplification primer complementary to the HIV nucleic acid, anchored to the plate at its 5' end, thereby leaving the 3' end available for extension by the action of a DNA polymerizing enzyme. The composite array is prepared by first arraying the probes, and then contacting the entire bottom surface of the well, including the arrayed portion, with a solution containing the amplification primer. Although different immobilization schemes may be used for this purpose, including immobilization by streptavidin-biotin interaction and covalent attachment, certain preferred embodiments use covalent attachment for both the probes and the primers.

A composite array typically has three components. First, there is a solid support which is characterized by a surface that is capable of receiving nucleic acids. Examples of useful solid supports include, but are not limited to, microscope slides or coverslips, dipsticks, optical fibers, beads, and multiwell plates. Multiwell plates and their equivalents are preferred solid supports because the well structures of the plate provide a convenient means for containing liquid reagents that later may be used for conducting nucleic acid amplification reactions. Moreover, a variety of multiwell plates are commercially available in different structural formats, including a choice of glass and plastic inner bottom surfaces. Second, there is at least one species of oligonucleotide primer immobilized to at least one surface of the solid support. Descriptions of the structural characteristics of useful primers are given elsewhere herein. Useful primers of the composite array may be attached to the solid support surface by any number of different approaches, including covalent and non-covalent bonding mechanisms. For example, the primers may be attached by noncovalent interactions (such as streptavidin-biotin interactions), or by covalent bonding (such as by thioester or amide bonds). Finally, composite arrays include at least one species of hybridization probe which typically is positioned on the surface of the solid support as a pattern of arrayed "spots" to result in a "probe array." The arrayed spots are deposited at discrete locations on the solid support surface such that one spot is spatially separated from another spot in the same array. Although composite arrays may include redundant spots of the same species of hybridization probe, it is preferred to employ at least two different species of hybridization probe. The working Examples presented herein describe arrayed spots of a single species of molecular beacon hybridization probe to illustrate the invention. However, in preferred embodiments more than one different hybridization probe is immobilized to the solid support, with each probe being present at a discrete spot separate from other probes. While the probes and primers of the composite array may be immobilized by different binding mechanisms, as may be true for a combination of probes immobilized by one type of covalent bond and primers immobilized by a different type of covalent bond, both the probes and primers conveniently may be linked to the solid support by the same type of bond. The immobilized probes and immobilized primers of the composite array also are subject to a preferred distribution pattern. More particularly, the immobilized primers preferably cover the surface of the composite array substantially uniformly except for binding sites on the surface that are occupied by immobilized probe molecules in the array pattern. Unlike the preferred separation of individual spots in the composite array, there is intended to be no spatial separation between the arrayed probes and the immobilized primers. Sites on the solid support surface of the composite array that are not occupied by bonds to the immobilized hybridization probes desirably are occupied by bonds to oligonucleotide primers, thereby resulting in a substantially uniform distribution of primers over the surface of the composite array.

Manufacturing of composite arrays involves contacting a probe array with an oligonucleotide-containing composition so that oligonucleotides become immobilized to the surface of the probe array at sites that are not occupied by immobilized probe molecules. To function as primers in nucleic acid amplification reactions, the oligonucleotides should be immobilized such that the 3'-ends are available to participate in template-dependent primer extension reactions. The probe array used in the construction of a composite array may be obtained from a commercial source as a pre-formed array, or alternatively may be constructed using the procedures illustrated herein.

In either case, oligonucleotide primers conveniently may be immobilized to the solid support surface of the probe array by immersion in a liquid composition that includes the oligonucleotides that are to be immobilized. By "immersion" or "immersing" is meant contacting the probe array with an excess of primer-containing liquid composition so that the surface of the probe array is fully contacted or covered by the liquid composition. It is unnecessary to exclude from contact with the primer-containing composition any part of the probe array occupied by immobilized probe molecules. Stated differently, it is preferred to promote contact between the primer-containing composition and the portion of the probe array that is occupied by probe molecules. It should be understood that it is unnecessary to immerse or submerge the entire solid support structure which contains the probe array. Instead, for example, if a probe array is formed on the inner bottom surface of a microtiter well, pipetting into the well an amount of the primer-containing composition sufficient to cover the bottom of the well would be adequate to accomplish immersion of the probe array. This advantageously avoids the need to deposit probe molecules using complex arraying machinery, and so simplifies construction of the composite array.

Kits for conducting nucleic acid amplification reactions using a composite array typically include a composite array in packaged combination with a soluble oligonucleotide primer. This soluble primer, when used in conjunction with primers immobilized on the surface of the composite array, can amplify an analyte nucleic acid from a test sample in an amplification reaction to produce analyte amplicons. These analyte amplicons can hybridize to, and so be detected by, one of the immobilized probes of the composite array. The kit also may contain a positive control nucleic acid that can be amplified by the same primers, but that can be detected by a probe in the composite array that is different from the probe used for detecting the analyte amplicon. Thus, detection of amplification products of the positive control nucleic acid can serve to verify that an amplification reaction has taken place. The kit may optionally contain an enzyme having DNA-dependent DNA polymerase activity and/or an enzyme having RNA-dependent DNA polymerase activity. However, these enzyme reagents may alternatively be packaged separately due to special handling requirements, such as the need for low temperature storage conditions.

Instrumentation for Making and Using Arrays

Microarray fabrication technology is now sufficiently advanced that devices useful for creating arrays by deposition of pre-formed nucleic acids are commercially available. For example, mechanical or robotic microspotting devices may be purchased from GeneMachines (San Carlos, Calif.), BioRobotics Ltd. (Cambridge, UK), Cartesian Technologies, Inc. (Irvine, Calif.), and Packard BioScience Co. (Meriden, Conn.). These devices enable one to produce arrayed spots of molecular beacons or other polynucleotides or other biomolecules on planar surfaces.

Alternative array formats which may be used in connection with the present invention involve optical fibers or microspheres. For example, optical fiber-based nucleic acid detectors of the type described in published International Application PCT/US00/13753, entitled, "Combinatorial Decoding of Random Nucleic Acid Arrays" represent non-planar array formats that easily can be adapted to accommodate combinations of arrayed probes and uniformly distributed primers. Compositions and methods employing oligonucleotide probes coupled to microspheres which can be adapted for use in connection with the present invention are disclosed in U.S. Pat. No. 6,057,107.

Devices for detecting fluorescent signals emitted by arrayed molecular beacons also are commercially available. For example, scanners for analyzing the results of hybridized arrays may be purchased from Molecular Dynamics (Piscataway, N.J.).

Useful Amplification Methods

Amplification methods useful in connection with the present invention include: transcription associated amplification techniques such as Transcription Mediated Amplification (TMA) and Nucleic Acid Sequence-Based Amplification (NASBA); the Polymerase Chain Reaction (PCR); Strand Displacement Amplification (SDA); and amplification methods using self-replicating polynucleotide molecules and replication enzymes such as MDV-1 RNA and Q-beta replicase. Methods for carrying out these various amplification techniques respectively can be found in U.S. Pat. No. 5,399,491, published European patent application EP 0 525 882, U.S. Pat. Nos. 4,965,188, 5,455,166, 5,472,840 and Lizardi et al., *BioTechnology* 6:1197 (1988). The disclosures of these documents which describe how to perform nucleic acid amplification reactions are hereby incorporated by reference.

In a preferred embodiment of the invention, nucleic acid sequences are amplified using transcription associated amplification techniques, and in a highly preferred embodiment the transcription associated amplification technique involves a TMA protocol. According to the TMA protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the target DNA at a defined site. Reverse transcriptase creates a complementary DNA copy of the target DNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule, including an inserted double-stranded promoter sequence. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can give rise to 100-1,000 copies of RNA amplicon, this expansion can result in the production of 10 billion amplicons from as little as 100 target molecules in less than one hour. The entire process is autocatalytic and is performed at a constant temperature.

Structural Features of Primers

As indicated above, a "primer" refers to an optionally modified oligonucleotide which is capable of hybridizing to a template nucleic acid and which has a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3' end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified (e.g., by the addition of propyne groups), as long as the modified base moiety retains the ability to form a non-covalent association with G, A, C, T or U, and as long as an oligonucleotide comprising at least one modified nucleotide base moiety is not sterically prevented from hybridizing with a single-stranded nucleic acid. As indicated below in connection with the chemical composition of useful probes, the nitrogenous bases of primers in accordance with the invention may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., N$^4$-methyl deoxyguanosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT No. WO 93/13121) and "abasic" residues where the backbone includes no nitrogenous base for one or more residues of the polymer (see Arnold et al., U.S. Pat. No. 5,585,481). Common sugar moieties that comprise the primer backbone include ribose and deoxyribose, although 2'-O-methyl ribose (OMe), halogenated sugars, and other modified sugar moieties may also be used. Usually, the linking group of the primer backbone is a phosphorus-containing moiety, most commonly a phosphodiester linkage, although other linkages, such as, for example, phosphorothioates, phosphoramidates, methylphosphonates, and non-phosphorus-containing linkages such as peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published PCT No. WO 98/57158, the disclosures of which are hereby incorporated by reference. Redox active moieties useful as labels in the present invention include various oxidation states of transition metals such as Cd, Cu, Co, Pd, Zn, Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). A preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Particularly preferred chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE.

In some applications, probes exhibiting at least some degree of self-complementarity are desirable to facilitate detection of probe:target duplexes in a test sample without first requiring the removal of unhybridized probe prior to detection. By way of example, structures referred to as "Molecular Torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., fluorophore/quencher) positioned so that a different signal is produced when the Molecular Torch is self-hybridized as opposed to when the Molecular Torch is hybridized to a target nucleic acid, thereby permitting detection of probe:target duplexes in a test sample in the presence of unhybridized probe having a viable label associated therewith. Molecular Torches are fully described in U.S. Pat. No. 6,361,945, the disclosure of which is hereby incorporated by reference.

Another example of a self-complementary hybridization assay probe that may be used in conjunction with the invention is a structure commonly referred to as a "molecular beacon." Molecular beacons comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open confirmation. The shift to the open confirmation is detectable due to reduced interaction of the label pair, which may be, for example, a fluorophore and a quencher (e.g., fluorescein or Cy5 and DABCYL). Methods of making and using molecular beacons are fully described in U.S. Pat. Nos. 5,925,517 and 6,150,097, the disclosure of which is hereby incorporated by reference. Molecular beacons useful for detecting target-specific nucleic acid sequences may be created by appending to either end of one of the probe sequences disclosed herein, a first nucleic acid arm comprising a fluorophore and a second nucleic acid arm comprising a quencher moiety. In this configuration, the target-specific probe sequence disclosed herein serves as the target-complementary "loop" portion of the resulting molecular beacon. Since unhybridized molecular beacons do not fluoresce substantially, it is not necessary to separate them from hybridized probe-target duplexes to detect the probe-binding event.

Yet another example of a self-complementary hybridization assay probe that may be used in conjunction with the invention is the "wavelength-shifting probe" as disclosed in U.S. Pat. No. 6,037,130, the disclosure of this patent being incorporated by reference herein in its entirety. Like molecular torches and molecular beacons, wavelength-shifting probes also include fluorophore and quencher moieties. Most conventionally, wavelength-shifting probes are interactively labeled, hairpin-forming oligonucleotides comprising stem-and-loop structures.

Synthetic techniques and methods of bonding labels to nucleic acids and detecting labels are well known in the art (e.g., see Sambrook et al., *Molecular Cloning, A Laboratory Manual,* 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333, Becker et al., European Patent App. No. 0 747 706 and Banerjee et al., in published International Application No. WO 01/44507).

Chemical Composition of Probes

Probes in accordance with the invention comprise polynucleotides or polynucleotide analogs and may carry a detectable label covalently bonded thereto. Nucleosides or nucleoside analogs of the probe comprise nitrogenous heterocyclic bases, or base analogs, where the nucleosides are linked together, for example by phosphodiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide bonds (sometimes referred to as "peptide nucleic acids" as described by Hyldig-Nielsen et al., PCT No. WO 95/32305), phosphorothioate linkages, phosphoramidate linkages, methylphosphonate linkages or combinations thereof. Sugar moieties of the probe may be either ribose or deoxyribose, or similar compounds having known substitutions, such as, for example, 2'-O-methyl ribose and 2'-halide ribose substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines (see, Cook, PCT No. WO 93/13121) and "abasic" residues where the backbone includes no nitrogenous base for one or more residues of the polymer (see Arnold et al., U.S. Pat. No. 5,585,481). A nucleic acid may comprise only conventional sugars, bases and linkages found in RNA and DNA, or may include both conventional components and substitutions (e.g., conventional bases linked via a methoxy backbone, or a nucleic acid including conventional bases and one or more base analogs).

Immobilization Chemistries

The mechanism underlying the invented immobilization chemistry involves increasing the reactivity of otherwise poor leaving groups on an oligonucleotide, and allowing the activated oligonucleotide to react with strong nucleophilic moieties that are disposed on a surface. Poor leaving groups, such as carboxylate or phosphate oxyanions, may be activated by forming a covalent bond with the carbodiimide moiety of 1-[3-(dimethylamino)propyl]-3-ethylcarbodiimide hydrochloride ("EDAC" hereafter). An alternative agent which may be used for activating poor leaving groups, and which falls within the scope of the invention, is 1-cyclohexyl-3-(2-morpholinoethyl) carbodiimide ("CMC" hereafter). Still another agent for activating poor leaving groups is N,N'-carbonyldiimidazole ("CDI" hereafter). If they are not already present, strong nucleophilic groups may be introduced onto a glass surface by reaction with a mercapto silane. Simply stated, a highly preferred approach uses a sulfhydryl-derivatized surface to form covalent bonds with carboxylated oligonucleotides after esterification of the carboxy moiety with EDAC or a similar activator.

Figure 1B:
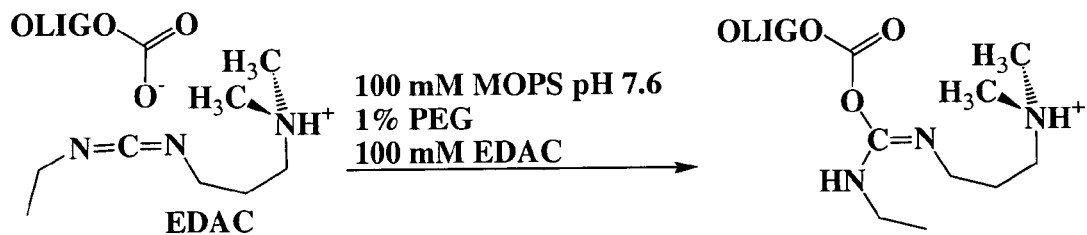
Figure 1C:
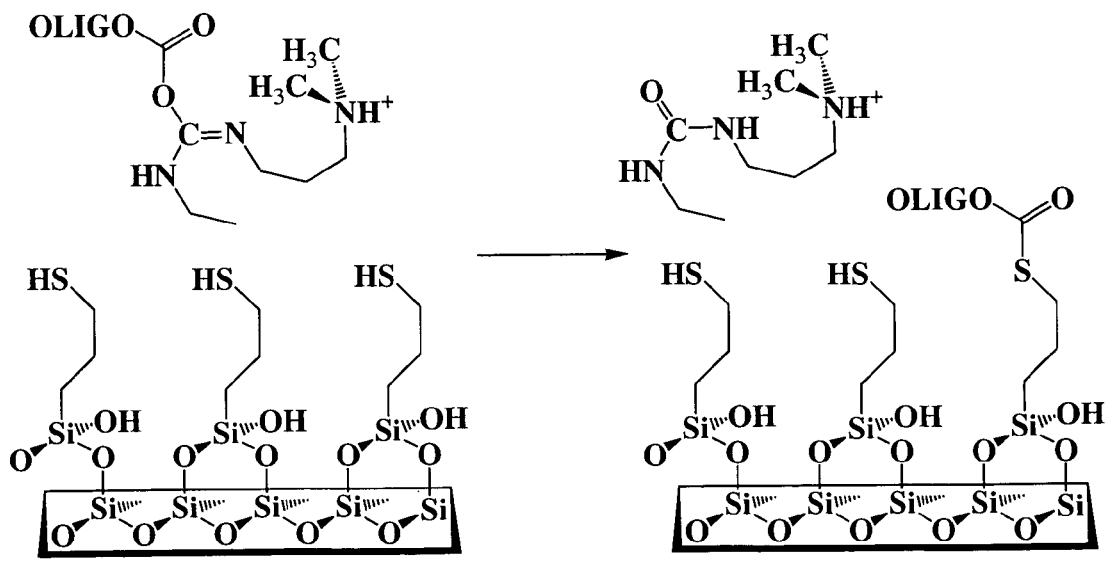

Possible reaction mechanisms which underlie the methods of the present invention are shown in FIGS. 1A-1C. FIG. 1A shows the reaction by which a glass surface may be functionalized with sulfhydryl moieties following treatment with 3-mercaptopropyltrimethoxysilane (3MPS). FIG. 1B shows how an oligonucleotide modified to include a carboxylate moiety can be allowed to react with EDAC to result in an esterified oligonucleotide. FIG. 1C shows how the sulfur atom of the glass-linked sulfhydryl moiety can react with the esterified oligonucleotide to immobilize the oligonucleotide.

The disclosed EDAC-catalyzed chemistry for coupling oligonucleotides to sulfhydryl-derivatized surfaces was shown to be highly tolerant of changes in reaction conditions. Although most of the coupling reactions carried out during development of the invention were performed in the presence of 100 mM MOPS buffer (pH 7.6), the concentration of the buffer was varied over a range of from 20-300 mM with good results. Moreover, numerous amine-based buffers (MOPS (3-(N-morpholino)propanesulphonic acid), MES (2-(N-morpholino)ethanesulphonic acid), HEPES (N-2-hydroxyethylpiperazine-N'-2-ethanesulphonic acid), CHES (3-(cyclohexlamino)ethanesulphonic acid), TAPS (tris (hydroxymethyl)methylaminopropanesulphonic acid), PIPES (piperazine-N,N'-bis(2-ethanesulphonic acid), Tris (tris(hydroxymethyl)aminomethane), and imidazole) were effective when used during the coupling reaction. Surprisingly, buffers based on phosphate, borate, and carbonate also led to advantageously high S/N readings, a measure that indicated highly efficient coupling. The concentration of the EDAC catalyst was varied over a range of at least 50-200 mM with good coupling results that were indicated by high S/N values. The presence of DMSO (dimethyl sulfoxide), TWEEN-20 (a registered trademark of ICI Americas, Inc., indicating polyoxyethylene(20)sorbitan monolaurate), PEG 3350 (polyethylene glycol having an average molecular weight of about 3,350 g/mole), $MgCl_2$ and $MnCl_2$ did not affect the oligonucleotide coupling reaction adversely. Increasing the concentration of the EDAC-activated oligonucleotide over a range of from 0.25-10 µM advantageously increased the S/N values on both sulfhydryl-derivatized and amine-derivatized glass surfaces.

In addition to the highly preferred coupling of oligonucleotides to solid surfaces, a variety of different biomolecules also were coupled to sulfhydryl-derivatized surfaces following EDAC activation. For example, S/N values of 30-75 were measured after activating a dextran-FITC conjugate by reaction with EDAC, contacting the activated molecule with mercapto silanized glass, and detecting the immobilized molecule by fluorescence. This showed that carbohydrates were efficiently immobilized to a surface following EDAC activation. In another instance, S/N values in the range of 35-75 were measured after reacting Angiotensin II-FITC (an eight-amino acid peptide conjugated to fluorescein isothiocyanate) with EDAC, contacting the activated molecule with mercapto silanized glass, and detecting the immobilized molecule. This showed that peptides were efficiently immobilized to a surface following EDAC activation. In contrast, BSA-FITC yielded a low, but measurable S/N of 1.9 when immobilized on a sulfhydryl-derivatized surface.

As detailed below, the invented chemistry has been used for immobilizing model oligonucleotides on planar glass surfaces, as well as on glass and polystyrene microparticles. Importantly, S/N values determined for oligonucleotide immobilization on glass microparticles derivatized with 3MPS was very high (about 700), thereby indicating highly efficient coupling. This contrasts to the same type of microparticles that were derivatized with amino silane, leading to S/N values of about 21, due largely to a significantly increased nonspecific binding level. Interestingly, underivatized glass microparticles efficiently coupled EDAC-activated oligonucleotides, likely through hydroxyl moieties that were naturally present on the surface of the glass, and that acted as strong nucleophiles. Polystyrene microparticles derivatized with sulfhydryl moieties yielded intermediate S/N values of about 51, and may reflect the approximately 50-fold lower nominal surface area of the polystyrene microparticles relative to the glass microparticles. Since polystyrene microparticles and planar and microparticle glass surfaces all yielded good S/N values when EDAC-activated fluorescently-labeled oligonucleotides were coupled to the surface-disposed sulfhydryl residues, it reasonably follows that planar sulfhydryl-derivatized polystyrene surfaces also can be coupled to EDAC activated oligonucleotides using the same, efficient chemistry.

Although certain applications employing covalently immobilized oligonucleotides naturally will depend on stability of the chemical linkage, other applications will benefit from the ability to chemically release the bound oligonucleotides without degrading the released oligonucleotides. It was in connection with this aspect of the invention that reversibility of oligonucleotide immobilization by hydrolysis of the bond joining an oligonucleotide and a solid support was examined by exposing samples of glass-immobilized oligonucleotides to a range of alkaline solutions. Increasing the pH from mild conditions that included soaking for 15 minutes in a pH 8.0 buffer to soaking in 0.005 N NaOH (pH 11.8) led to an approximately 10-fold reduction in the baseline S/N value after 5 minutes, and an approximately 45-fold reduction in S/N after 15 minutes. Increasing the alkalinity to the range of pH 13-14 did not lead to further substantial reductions in S/N values. These results confirmed that immobilization of oligonucleotides by the procedure described herein represented a stable attachment under the conditions encountered during conventional hybridization and detection procedures, but that the covalent bond could be reversed simply by exposure to highly alkaline conditions. While not wishing to be bound by any particular theory, it is believed that the invented method of chemically joining a carboxylated oligonucleotide and a solid surface displaying sulfhydryl moieties results in the formation of a thioester linkage, as shown in FIG. 1C.

The immobilization chemistry described herein advantageously was highly robust. Indeed, numerous variables related to the silanization procedure were changed without compromising the efficiency of oligonucleotide coupling, thereby suggesting that these steps were not critical to the success of the invention. For example, the glass surface to be silanized and coupled with an oligonucleotide may first be cleaned using any of several different cleaning solutions, including aqueous 10% $H_2O_2$ and 50% MeOH in water with 10% $H_2O_2$. The amount of silane in the silanization reaction can be varied from at least 2-6% dissolved in 90% MeOH with similarly good results measured after coupling a fluorescently labeled oligonucleotide using the EDAC-based chemistry described herein. Holding the silane concentration constant at 4%, the fraction of organic solvent could be varied from 0-96% with no detrimental effects. Additionally, oligonucleotides to be immobilized may comprise DNA, RNA, or nucleic acids having 2'-OMe backbones or other modifications.

Glass surfaces intended for coupling with oligonucleotides according to the methods described herein were chemically activated using functionalized silanes. However, if the surface comprises naturally disposed hydroxyl or sulfhydryl moieties, then no additional modification by silanization should be necessary for success of the coupling reaction, a fact that is supported below by results obtained using glass microparticles. Conventional protocols for silanization employ silanes dissolved in substantially organic solvents (e.g. 25% silane in dry xylene, Lamture et al., *Nucleic Acids Res.* 1994, 22, 2121-2125; 1% silane in toluene, Möller et al., *Nucleic Acids Res.* 2000, 28, e91; 3% silane in 95% methanol, Beier and Hoheisel, *Nucleic Acids Res.* 1999, 27, 1970-1977; 2% silane in 90% methanol/$H_2O$ Zammatteo et al., *Anal. Biochem.* 2000, 280, 143-150; 1% silane in 95% acetone/$H_2O$, Guo et al., *Nucleic Acids Res.* 1994, 22, 5456-5465; 2% silane in 50% acetone/$H_2O$, Aebersold et al., *Anal. Biochem.* 1990, 187, 56-65). Most of the silanization procedures conducted during development of the invention were performed using 4% silane dissolved in 90% methanol/water. However, the following procedures indicated that effective silanization could be achieved even under substantially aqueous conditions.

Example 1 describes the procedures that demonstrated a variety of silanization conditions could be used for modifying glass surfaces in preparation for covalent coupling of oligonucleotides.

EXAMPLE 1

Efficient Introduction of Nucleophiles onto Glass Surfaces

Glass-bottomed polystyrene 96-well plates (Whatman Polyfiltronics; Rockland, Mass.) were cleaned by soaking in a solution of 10% $H_2O_2$/50% MeOH in water for 30 minutes at room temperature, washed with water three times using an automated plate washer, and then dried in a vacuum desiccator for at least 2 hours. Cleaned and dried plates were contacted with 100 μl per well of different concentrations of 3-(mercaptopropyl)trimethoxysilane (3MPS) in various solvent mixtures for different times at room temperature (about 23° C.), washed manually three times with 100 μl of 90% MeOH, washed three times with 100 μl water using the automated plate washer, and then vacuum desiccated overnight. Wells (n=12) from the 120 minute time point were used subsequently for studying nonspecific binding. Coupling reactions were carried out by contacting the silanized surfaces for 60 minutes at room temperature with 25 pmol of a synthetic oligonucleotide representing the hereditary hemochromatosis mutation model and having the sequence GATATACGTGCCAGGTGGAG (SEQ ID NO: 1), including a carboxylate dT adduct joined to the 5' hydroxyl of the oligonucleotide by an 18 atom glycol linker, and a fluorescein moiety joined at the 3' end. The carboxylated dT moiety was a phosphoramidite oligonucleotide precursor that had been purchased from Glen Research Corporation (Sterling, Va.). The oligonucleotide was contained in 100 μl of a solution of 0.1 M MOPS buffer (pH 7.6), 1% PEG 3350, and 0.1 M EDAC. Control reactions for monitoring nonspecific binding omitted EDAC. After the indicated times, the chemically modified wells were soaked for 15 minutes in 100 μl of 1× TENT buffer (50 mM Tris (pH 8.0), 0.1 mM EDTA, 50 mM NaCl, and 0.2% TWEEN-20), and then washed three times and filled with 100 μl of the same buffer. Fluorescence signals were read from the bottom of the plate using a Molecular Dynamics TYPHOON 8600 flatbed fluorescence scanner. Plate surfaces were excited at 532 nm, and fluorescent emissions from immobilized oligonucleotides were read at 526 nm. Mean fluorescence intensities (±SD) were sampled from a $1.41 \times 10^7$ μm$^2$ circular area on the bottom of the plate for each sample. Corrected S/N values were calculated by subtracting background fluorescence from the specific fluorescence measurement, and dividing the result by the nonspecific fluorescence after subtraction of background fluorescence. The mean background±standard deviation was 50.8±1.75 for 6 trials.

Figure 2A:
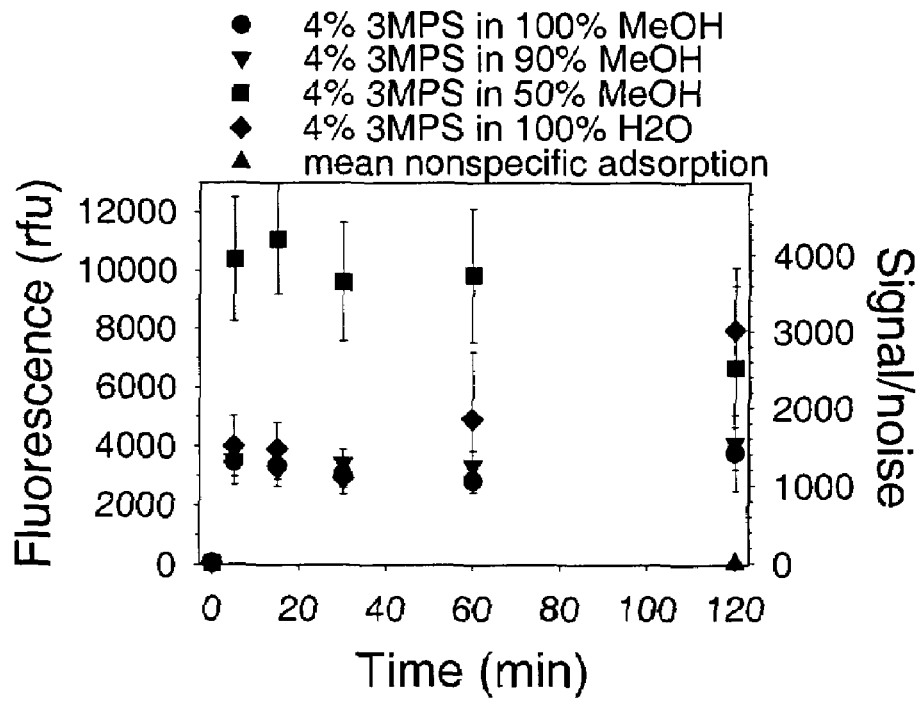
FIGS. 2A-2B are graphs relating silanization reaction time with a measure of oligonucleotide immobilization.
Figure 2B:
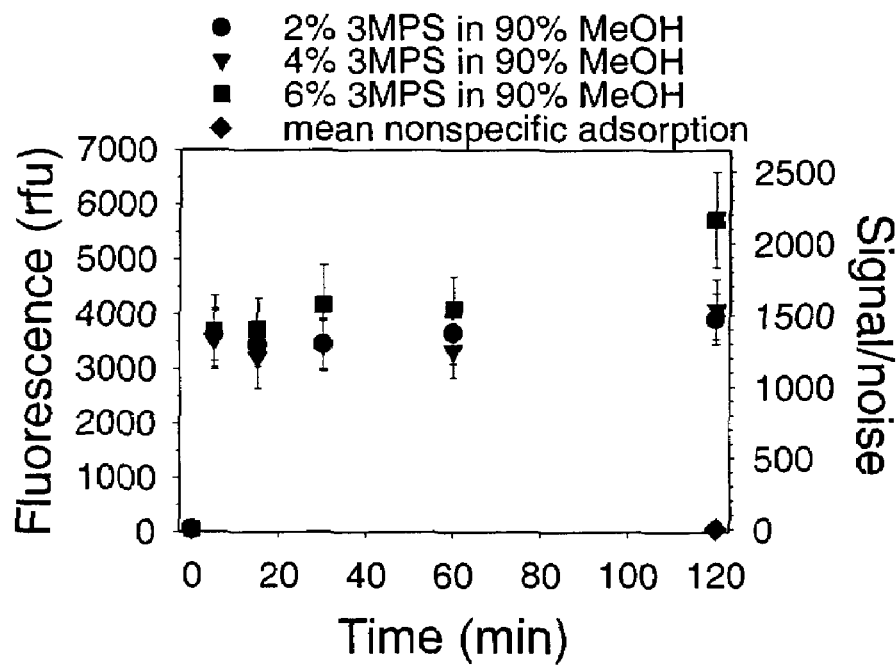

FIG. 2A shows that substantially similar results were obtained when 96% methanol, 90% methanol and 96% water were used as solvents for silanization with 3MPS for reaction times ranging from 5-60 minutes. Interestingly, treatment with 3MPS dissolved in an intermediate methanol concentration of 50% yielded superior subsequent oligonucleotide coupling. Despite the poor water solubility of 3MPS, as judged by turbidity of the solution, silanization with 3MPS in water gave good results while avoiding the need for organic solvents entirely. The results presented in FIG. 2B show that the concentration of silane had only a minimal effect on subsequent covalent coupling.

Additional procedures were carried out to illustrate the general utility of the coupling chemistry disclosed herein. More specifically, the experimental description which follows illustrates how the coupling reaction was used for linking oligonucleotides to microparticles composed of glass or polystyrene.

Example 2 describes the procedures that demonstrated how bond formation by activation of carboxy-terminal oligonucleotides followed by reaction with sulfhydryl-derivatized glass and polystyrene microparticle surfaces was very efficient.

EXAMPLE 2

Coupling Oligonucleotides to Glass or Plastic Microparticles

Batches of magnetic porous glass (MPG) 5 μm microparticles obtained from CPG, Inc., (Lincoln Park, N.J.) were allowed to react with 3MPS or γ-aminopropyltrimethoxysilane (GAPS) and subsequently coupled with a fluorescent oligonucleotide. In this procedure GAPS was used for introducing functional amine groups instead of sulfhydryl groups onto different surfaces. Uncoated 5 μm Magnetic Porous Glass microparticles had nominal surface areas of 314 μm$^2$ per particle. Sulfhydryl derivatized 1.46 μm ESTAPOR polystyrene magnetic microparticles from Merck Eurolab S.A., (France) had nominal surface areas of 6.70 μm$^2$ per particle. Using either $3.60 \times 10^6$ glass or $1.69 \times 10^8$ polystyrene microparticles per ml, samples were washed 3 times using 1 ml volumes of 90% MeOH, and placed in vacuum desiccator to dry. Separate aliquots of glass microparticles were suspended in 4% 3MPS or GAPS dissolved in 90% MeOH, incubated for 2 hours with periodic vortexing to maintain particle suspension, washed three times using 1 ml of 90% MeOH, and dried in the vacuum desiccator. Duplicate coupling reactions were performed substantially as described above, using 250 pmol of the carboxylated and fluorescein-labeled oligonucleotide from Example 1 in 1 ml of a solution of 0.1 M MOPS (pH 7.6), 1% PEG, and 0.1 M EDAC for 2 hours at room temperature, also with periodic resuspension. EDAC was omitted from the nonspecific control reactions, and no oligonucleotide was added to the background control reactions. Microparticles having sulfhydryl moieties disposed thereon were soaked in 1 ml 1× TENT buffer at room temperature for at least 15 minutes. Microparticles having surface-disposed amine groups were soaked in 0.4 N NaOH, 0.1 mM EDTA, 50 mM NaCl, and 0.2% TWEEN-20 for 15 minutes. In both instances, the microparticles were washed 3 times using 1 ml of 1× TENT buffer at room temperature, and taken up in 1 ml of 1× TENT buffer. Selected specific reactions were repeated on the next day to test day-to-day variation. Nonspecific and background values were assumed to be similar to those measured during the first trial. Coupling efficiencies were compared after measuring fluorescent signals on the microparticles by fluorescence-activated cell sorting (FACS) using a FACSCAN machine (Becton, Dickinson and Company; Franklin Lakes, N.J.). Fluorescence data was obtained for 2,500-10,000 events. S/N values were calculated as described above from the averages of duplicate measurements.

available for coupling to the polystyrene microparticle when compared with the larger and more porous glass microparticles which, based on diameter, have roughly 50-fold more surface area than the polystyrene microparticles. Finally, glass microparticles derivatized with 3MPS coupled to a carboxy-terminal oligonucleotide substantially more efficiently and specifically than did a comparable microparticle derivatized with GAPS. The lower S/N observed with the GAPS-derivatized surface was due to both increased nonspecific adsorption and to lower specific coupling yields.

TABLE 1

Coupling an Oligonucleotide to Glass and Polystyrene Microparticle Surfaces

| Particle Type | Surface | Coupling | Mean rfu | Corrected S/N |
|---|---|---|---|---|
| glass | sulfhydryl | (bkgd) no oligo | 7.6 | |
| glass | sulfhydryl | (bkgd) no oligo | 6.5 | |
| glass | sulfhydryl | (nonspecific) oligo, no EDAC | 12.0 | |
| glass | sulfhydryl | (nonspecific) oligo, no EDAC | 24.9 | |
| glass | sulfhydryl | (specific) oligo, EDAC, day 1 | 7256 | 640 |
| glass | sulfhydryl | (specific) oligo, EDAC, day 1 | 7347 | |
| glass | sulfhydryl | (specific) oligo, EDAC, day 2 | 7659 | 740 |
| glass | sulfhydryl | (specific) oligo, EDAC, day 2 | 9104 | |
| glass | amino | (bkgd) no oligo | 3.8 | |
| glass | amino | (bkgd) no oligo | 9.7 | |
| glass | amino | (nonspecific) oligo, no EDAC | 56.4 | |
| glass | amino | (nonspecific) oligo, no EDAC | 59.8 | |
| glass | amino | (specific) oligo, EDAC, day 1 | 1143 | 22 |
| glass | amino | (specific) oligo, EDAC, day 1 | 1075 | |
| glass | underivatized | (bkgd) no oligo | 4.9 | |
| glass | underivatized | (bkgd) no oligo | 5.3 | |
| glass | underivatized | (nonspecific) oligo, no EDAC | 18.4 | |
| glass | underivatized | (nonspecific) oligo, no EDAC | 20.9 | |
| glass | underivatized | (specific) oligo, EDAC, day 1 | 6772 | 460 |
| glass | underivatized | (specific) oligo, EDAC, day 1 | 6751 | |
| polystyrene | sulfhydryl | (bkgd) no oligo | 5.4 | |
| polystyrene | sulfhydryl | (bkgd) no oligo | 6.2 | |
| polystyrene | sulfhydryl | (nonspecific) oligo, no EDAC | 6.8 | |
| polystyrene | sulfhydryl | (nonspecific) oligo, no EDAC | 10.4 | |
| polystyrene | sulfhydryl | (specific) oligo, EDAC, day 1 | 139.5 | 51 |
| polystyrene | sulfhydryl | (specific) oligo, EDAC, day 1 | 157.0 | |
| polystyrene | sulfhydryl | (specific) oligo, EDAC, day 2 | 34.9 | 10 |
| polystyrene | sulfhydryl | (specific) oligo, EDAC, day 2 | 33.2 | |

The results presented in Table 1 indicated that sulfhydryl-modified glass particles coupled to the model oligonucleotide with superior efficiency. Fluorescence signals presented in the table are given in relative fluorescence units (rfu). Interestingly, oligonucleotide coupling to untreated glass microparticles also yielded advantageously high S/N values, thereby indicating the formation of a chemical bond between hydroxyl moieties of the glass surface and the EDAC-activated oligonucleotide. This alternative route for coupling oligonucleotides directly to glass is embraced within the scope of the present invention. Thus, a hydroxy-functionalized surface, such as glass or hydroxy-terminal silane-derivatized glass, can be reacted with EDAC-activated oligonucleotides using the methods disclosed herein to immobilize the oligonucleotides. The results further showed that EDAC-activated oligonucleotides coupled to polystyrene microparticles with acceptable, although somewhat lower coupling efficiencies as judged by the S/N values appearing in Table 1. Compared with the superior results obtained using the glass microparticles, the relatively decreased S/N values measured for the polystyrene microparticles was largely due to reduced signals rather than increased background and nonspecific adsorption. This may be due to a reduced number of sulfhydryl sites Example 3 describes the procedures that addressed the effect on covalent coupling of variables that included the type of buffer that was used in the coupling reaction and the breadth of the useful pH range over which efficient coupling to a sulfhydryl surface may take place. The results confirmed that immobilization of an oligonucleotide took place over a broad pH range, and in the presence of many different buffer types. More specifically, the results which follow demonstrated that coupling of a carboxy-terminal oligo to a sulfhydryl-derivatized surface was substantially more effective than coupling of a carboxy-terminal oligomer to an amino-derivatized surface and had a wider pH tolerance and more general buffer dependence than the amino-derivatized surface.

EXAMPLE 3

Effect of pH Range and Buffer Type on Oligonucleotide Coupling

A glass-bottomed polystyrene 96 well plate was cleaned and then dried overnight as described under Example 1. Wells of the cleaned plate were contacted with 100 µl per well of 4% 3MPS or 4% GAPS dissolved in 90% MeOH at room temperature for 120 minutes, then washed manually three times with 90% MeOH, washed with an automated plate washer three times with water, and vacuum desiccated overnight. Wells from the 120 minute timepoint (n=12) were subsequently used for studying nonspecific binding of oligonucleotides. Coupling reactions were performed using 25 pmol of the carboxylated and fluoroscein-labeled oligonucleotide from Example 1 in 100 μl volumes of a solution made 0.1 M of the indicated buffer, 1% PEG, and 0.1 M EDAC for 60 minutes at room temperature. EDAC was omitted from control trials that monitored nonspecific reactions. Wells were soaked in 1× TENT buffer (for 3MPS-treated surfaces) or in a solution of 0.4 M NaOH, 0.1 mM EDTA, 50 mM NaCl and 0.2% TWEEN-20 (for GAPS-treated surfaces) at room temperature for at least 15 minutes before washing 3 times with 1× TENT buffer using the automated plate washer at room temperature, filling with 100 μl 1× TENT buffer, and reading fluorescence values, also as described under Example 1.

Figure 3A:
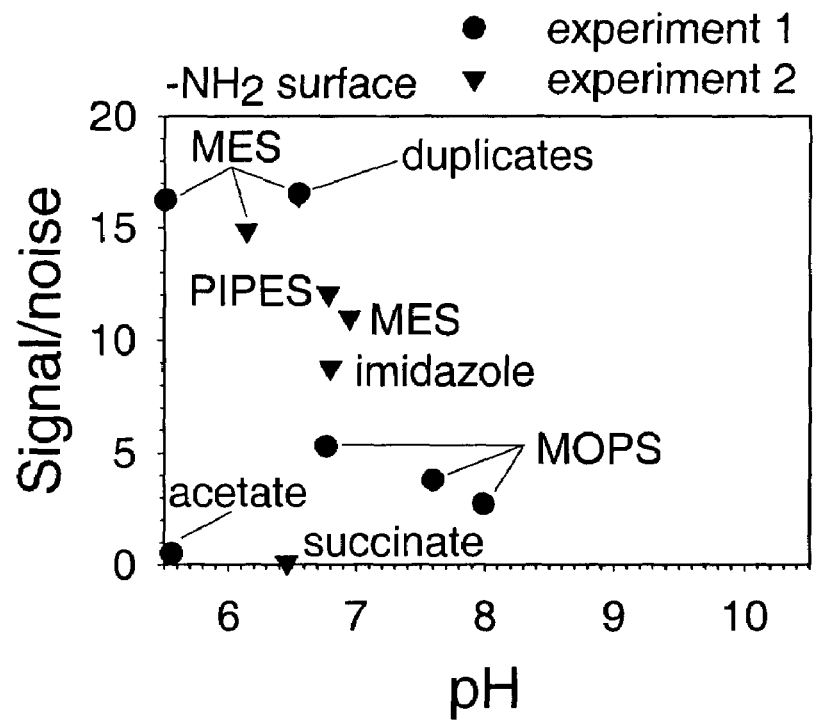
FIGS. 3A-3C are a series of graphs showing the effects of different buffer and pH conditions on oligonucleotide immobilization.
Figure 3B:
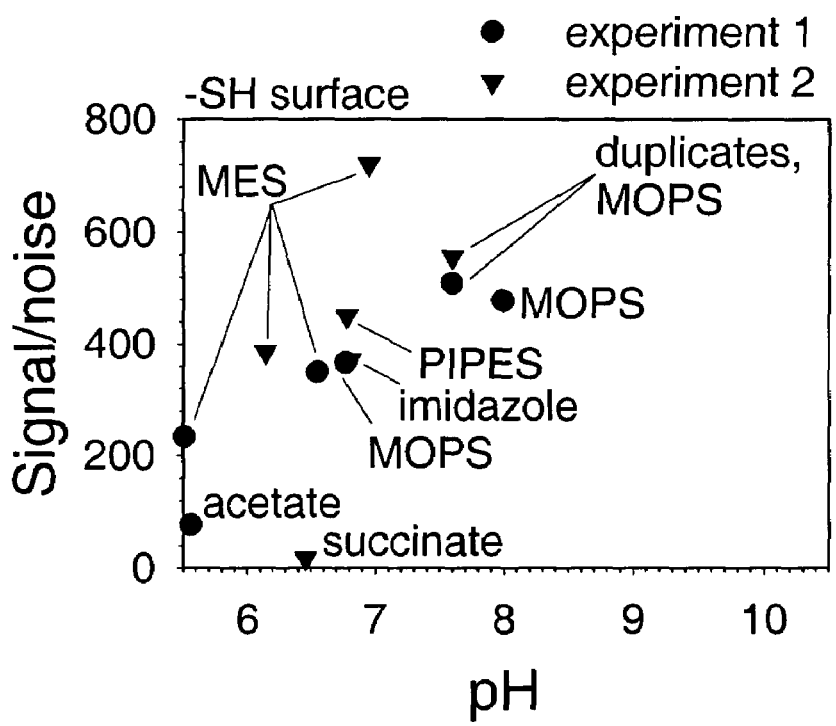
Figure 3C:
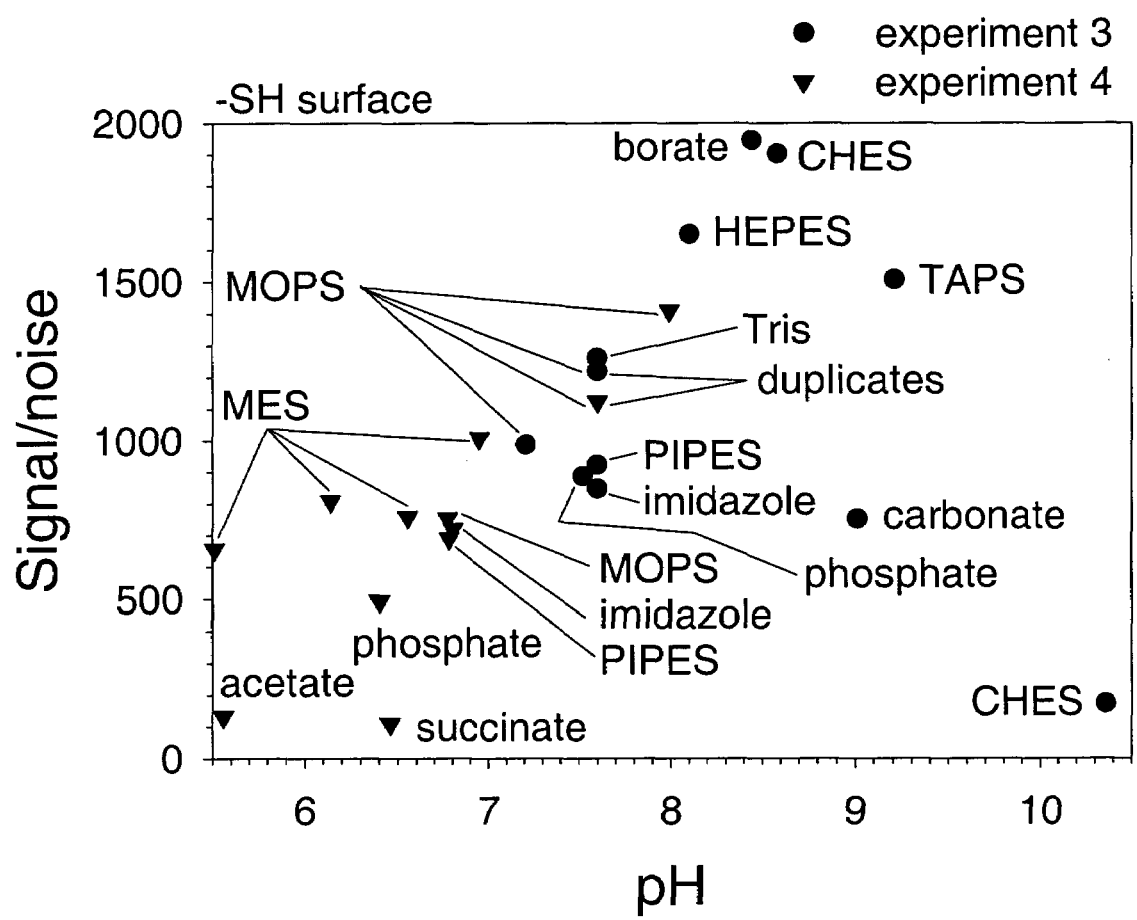

The results presented in FIGS. 3A-3C summarize four comparative experiments. Corrected S/N values were calculated as above, with mean backgrounds±standard deviation being 252±78.0, 51.2±1.56, and 49.6±1.45 rfu for 12 trials in FIGS. 3A-3C, respectively. Based on reproducibility of common control points in experiments 1 and 2 (see data points corresponding to MES (pH 6.55) and MOPS (pH 7.60) for the amino and sulfhydryl surfaces, respectively), these experiments were grouped together, as were experiments 3 and 4 for the same reasons. The enhanced S/N values observed in experiments 3 and 4, relative to experiments 1 and 2, likely were due to the use of a new lot of EDAC rather than any other variable. EDAC is known to decompose as a function of time following atmospheric exposure and hydration.

The results shown in the figure indicated that coupling of labeled EDAC-activated oligonucleotides to a sulfhydryl-derivatized surface yielded substantially higher S/N values when compared with coupling of the same oligonucleotides to an amino-derivatized surface. The useful pH range for coupling EDAC-activated oligonucleotides to sulfhydryl-derivatized surfaces was between about 5.5 and 9.5. Notably, use of borate or CHES buffers near pH 8.5 for oligonucleotide coupling led to S/N values of almost 2,000, or nearly twice that of the standard conditions (MOPS buffer at pH 7.6). While the best conditions for the amine-derivatized surfaces gave fluorescent signals that were comparable with the signals obtained for the best sulfhydryl-derivatized surfaces, background signals measured for the amino-derivatized surfaces were quite high while the background signals for the sulfhydryl-derivatized surfaces were very low. This may reflect nonspecific binding of negatively charged oligonucleotides to surface-disposed amino groups which may, under conditions of appropriate pH, take on a positive charge. Unexpectedly, coupling EDAC-ativated oligonucleotides to amino-derivatized surfaces exhibited a narrow useful pH range (≦5.5-7). This was surprising because amino moieties are characterized by a $pK_a$ in the range of about 10, and so it reasonably would be expected that coupling to the amino-derivatized surface should continue to improve at pH values greater than 10 when the amino group approaches a neutral, more nucleophilic state. Of course, at very high pH values, the rate of hydrolysis of an amide or thioester bond would compete significantly with the condensation reaction, thereby resulting in decreased yields of the desired product. Finally, the results also showed that the amino-derivatized surface was very sensitive to the type of buffer that was used, with the morpholino buffer MES being the most effective buffer over about a 1 pH unit range, and oxyanion buffers being least effective. Interestingly, the sulfhydryl-derivatized surfaces were relatively insensitive to buffer type, even to the point that several oxyanion buffers yielded high coupling efficiencies (e.g. borate, carbonate, phosphate).

The following section demonstrates that the coupling chemistry disclosed herein was useful for joining molecules other than oligonucleotides to derivatized glass. More specifically, the following procedures show how model carbohydrates, peptides and proteins can be attached to a glass surface. This was accomplished by succinylating with a fluorescein-conjugated carbohydrate, and then allowing carboxylate moieties on this molecule or fluorescein-conjugated peptide or protein to be activated by EDAC and then react with a sulfhydryl-derivatized glass surface.

Example 4 describes the procedures that were used to show that chemical bond formation led to efficient coupling of a variety of biomolecules to glass surfaces.

EXAMPLE 4

Coupling Biomolecules to Glass

Glass bottomed polystyrene multiwell plates were cleaned and silanized according to the method described under Example 1, except that glass surfaces were silanized with 4% 3MPS dissolved in 90% MeOH for 120 minutes at room temperature. Coupling reactions were carried out in a buffer that included 0.1 M MOPS (pH 7.60), 1% PEG, 0.1 M EDAC, together with various amounts of a fluorescein-conjugated model peptide, a fluorescein-conjugated model protein, or a succinylated, fluorescein-conjugated model carbohydrate for up to 120 minutes at room temperature. No EDAC was included in the control reactions that measured nonspecific binding and that were carried out for 120 minutes. S/N values were calculated at the 60 minute time points. The DNA oligonucleotide from Example 1 served as a positive control in the procedure to confirm integrity of the coupling reaction. The model carbohydrate used in the procedure was dextran-FITC having a molecular weight of about 4,400 g/mole; 2.5 mM dextran-FITC (polymer concentration) succinylated in 0.1 M phosphate buffer (pH 8.2), carbonate buffer (pH 10.0), or phosphate buffer (pH 12.3) in 1 ml $H_2O$ by adding 60 mg succinic anhydride (10-fold molar excess over glucose units) and incubating for 22 hours at room temperature in the dark. The reaction product was purified using a disposable spin column packed with a size-exclusion chromatography matrix using standard laboratory procedures that will be familiar to those having an ordinary level of skill in the art. A control procedure for coupling carbohydrate to glass was substantially identical to the foregoing, except that the "succinylation" reaction was performed in phosphate buffer (pH 8.2) without addition of succinic anhydride. The model peptide used in the procedure was Angiotensin II-FITC, having the sequence Asp-Arg-Val-Tyr-Ile-His-Pro-Phe (SEQ ID NO:2) and being labeled with FITC at the amino terminus. The model protein used in the procedure was bovine serum albumin (BSA)-FITC (having a molecular weight of about 71,100 g/mole and being labeled with 12 moles of FITC per mole of BSA). Values presented in Table 2 represent mean fluorescence (rfu) from a $7.98 \times 10^6$ μm$^2$ circular area. The mean background for 12 samples±SD was 54.0±1.52 rfu. Corrected S/N values were calculated as in FIG. 1 from averages of the duplicates.

The results presented in Table 2 indicated that a variety of carboxy-activated biomolecules, including nucleic acids, carbohydrates and peptides, were coupled to sulfhydryl-derivatized surfaces by chemical bond formation. Because each of the different biomolecule species had a different specific activity that was determined by the numbers of fluorescein and carboxylate functional groups disposed thereon, numerical values appearing in the table should not be compared between different types of biomolecules. Immobilization of the oligonucleotide gave a result in the expected 500-5000 S/N range, thereby confirming that EDAC-catalyzed coupling in the procedure had taken place. The succinyated dextran coupled with approximately equivalent efficiency under all of succinylation conditions tested, although succinylation in phosphate buffer at pH 12.3 gave somewhat higher noise levels. The fact that dextran without carboxylate moieties gave coupling above background may be due to the presence of uncharacterized carboxylate moieties on the source dextran or to an alternate EDAC-activated coupling chemistry between sulfhydryl and hydroxyl groups. The peptide coupled efficiently, but with increasing noise at higher peptide concentrations tested in the procedure. Finally, the model protein gave very high signal and noise levels, thereby leading to an S/N value that was low, but measurable. The high noise levels were not surprising because many proteins, including BSA, are known to exhibit nonspecific binding to glass and are routinely used as a nonspecific blocking agents. The addition of DTT to the wash solution of BSA-FITC did not improve the S/N values. In view of these successes, it reasonably follows that numerous other molecular species can be coupled to glass surfaces by chemical bond formation as illustrated herein.

TABLE 2

Coupling of Various Biomolecules to a Sulfhydryl-Derivatized Surface

| Condition | Concentration (µM) | Signal | Noise | Corrected S/N |
|---|---|---|---|---|
| carboxy terminal DNA oligomer | 0.25 | 2469 | 57.2 | 750 |
| carbohydrate, pH 8.2 succinylation | 2.5 | 1417 | 72.0 | 75.7 |
| carbohydrate, pH 10.0 succinylation | 2.5 | 1670 | 76.7 | 71.2 |
| carbohydrate, pH 12.3 succinylation | 2.5 | 1834 | 109.8 | 31.9 |
| carbohydrate | 2.5 | 120.6 | 55.6 | 41.6 |
| peptide | 2.5 | 2946 | 92.3 | 75.7 |
| peptide | 25 | 6841 | 245.7 | 35.4 |
| protein | 0.25 | 5726 | 3060 | 1.90 |

The utility of the immobilization chemistry disclosed herein was explored more fully by modifying the reaction scheme so that sulfhydryl or amine moieties were disposed on the biomolecules to be immobilized, and the surfaces that were to receive the biomolecules displayed carboxylate moieties that could be activated by reaction with EDAC. In this instance, 96-well plastic tissue culture plates were used as the surfaces for receiving either thiolated or aminated oligonucleotides that also were fluorescein-labeled.

Example 5 describes procedures that investigated the efficiency of alternative approaches for coupling sulfhydryl-derivatized or amine-derivatized oligonucleotides with surface-disposed carboxylate moieties.

EXAMPLE 5

Chemical Bond Formation Using Thiolated Oligonucleotides

Clear-bottomed polystyrene FALCON TC 96-well plates (purchased from Becton, Dickinson and Company) were prewashed essentially according to the method described under Example 1. These plates are known to display carboxylate moieties on their surfaces. Individual wells of the plate were contacted with a solution that included 0.1 M of one of three buffers, 0.1 M EDAC, and 0.25 µM of a synthetic oligonucleotide having the sequence of SEQ ID NO:1 and one of two reactive terminal groups for up to 120 minutes at room temperature. A reactive disulfide group was introduced at the 3' end of one oligonucleotide using phosphoramidite chemistry and a 3'-THIOL-MODIFIER C3 S-S CPG (Glen Research). A reactive amine was introduced at the 5' end of the other oligonucleotide using a 5'-AMINO-MODIFIER C6 (Glen Research). Fluorescein moieties were present in each of the oligonucleotides at the terminus opposite the reactive group. Preliminary experiments did not indicate any advantage from reducing the disulfide bond prior to surface coupling. EDAC was omitted from trials that served as controls for detecting nonspecific binding. The three buffers were MES buffer (pH 6.6), MOPS buffer (pH 6.8) and MOPS buffer (pH 7.6). S/N values were calculated at the 60 minute time points. After processing the plates as above, fluorescence measurements were taken as described under Example 1. Numerical values representing mean fluorescence (rfu) from a $7.98 \times 10^6$ µm$^2$ circular area of each well was determined. Mean background values±SD were 717±10.0 rfu for six trials.

These background values are substantially higher than those observed using glass surfaces, and are due to fluorescence from the plastic that was used. S/N values were calculated as in FIG. 1.

The results presented in Table 3 indicated that formation of chemical bonds between carboxylate-derivatized polystyrene surfaces and oligonucleotides having sulfhydryl moieties disposed thereon was substantially less efficient than the reversed reaction on glass. However, formation of amide bonds to carboxylate-derivatized polystyrene surfaces yielded results similar to the reversed reaction on glass due to low nonspecific adsorption even though specific coupling was low. The apparent nonspecific adsorption (noise) was higher for the sulfhydryl-linked oligonucleotide than for the amino-linked oligonucleotide. When making this comparison it must be kept in mind that the two different oligonucleotides used in the procedure had different specific activities. As a result, there was a somewhat higher S/N value for the amino-linked oligonucleotide than for the sulfhydryl-linked oligonucleotide.

TABLE 3

Coupling of Amine- and Sulfhydryl-Derivatized Oligonucleotides to Carboxylated Polystyrene Surfaces

| Plate Surface | Oligo-nucleotide | Buffer | Signal | Noise | Corrected S/N |
|---|---|---|---|---|---|
| COO⁻, prewashed | SH terminal | MES pH 6.6 | 895 | 752 | 5.1 |
| COO⁻, prewashed | SH terminal | MOPS pH 6.8 | 944 | 756 | 5.8 |
| COO⁻, prewashed | SH terminal | MOPS pH 7.6 | 959 | 747 | 8.1 |
| COO⁻, prewashed | NH$_2$ terminal | MES pH 6.6 | 1048 | 718 | 331 |
| COO⁻, prewashed | NH$_2$ terminal | MOPS pH 6.8 | 904 | 726 | 20.9 |
| COO⁻, prewashed | NH$_2$ terminal | MOPS pH 7.6 | 776 | 720 | 19.7 |

Example 6 describes the procedures that were used to demonstrate that only mild washing conditions are needed for processing solid supports following covalent coupling of biomolecules, and that conditions of high pH may be used to release the immobilized biomolecule. Thus, optimal washing conditions are advantageously very mild. In contrast, strongly denaturing conditions were needed to remove nonspecific, electrostatically adsorbed, negatively charged oligomers from the positively charged amino surface.

EXAMPLE 6

Releasing Immobilized Biomolecules by Chemical Bond Hydrolysis

Procedures for performing coupling reactions and immobilizing oligonucleotides on glass-bottomed multiwell plates were as described under Example 1, except that coupling reactions were carried out in the presence of 0.1 M MOPS (pH 7.6), 1% PEG, 0.1 M EDAC and 0.25 µM of the carboxylated and fluorescein-labeled oligonucleotide for 30 minutes at room temperature. EDAC was omitted from the trial that was used for assessing nonspecific binding reactions. All of the post-coupling wash solutions included 0.1 mM EDTA, 50 mM NaCl, and 0.2% TWEEN-20 for the indicated times. Variables tested in the procedure included the presence of 0.05 M Tris (pH 8.0) or 0.005-0.4 N NaOH, and the length of time the immobilized oligonucleotide was left in contact with the wash solution. Fluorescence readings were measured as described under Example 1 using a $1.41 \times 10^7$ µm$^2$ circular area. Mean background values±SD were 52.4±2.22 rfu for a sample size of 24. S/N values were calculated as described above.

The results presented in Table 4 indicated that very mild conditions, such as soaking in 1× TENT buffer for 15 minutes were sufficient to reduce nonspecific binding of oligonucleotides to near background levels, and that use of more denaturing conditions did not provide any advantage. The use of 1× TENT buffer as the wash solution gave very high specific signals and S/N values. In contrast, even the most mild of the alkaline hydroxide treatments significantly reduced both the specific signal and S/N. This reflected hydrolysis of the chemical bond between the solid support and the oligonucleotide, and was consistent with the finding that use of CHES buffer (pH 10.4) in the coupling conditions described in Example 3 yielded poor results. Indeed, those reaction conditions may have favored a higher degree of hydrolysis than coupling.

TABLE 4

Comparison of Post-Coupling Washing Solutions on S/N of Chemically Immobilized Oligonucleotides

| Solution | Time (min) | Signal | Noise | Corrected S/N |
| --- | --- | --- | --- | --- |
| 0.05 M Tris pH 8.0 (1 × TENT) | 15 | 5,522 | 52.7 | 18,000 |
| 0.005 N NaOH (pH 11.8) | 5 | 1,161 | 53.0 | 1,800 |
| 0.005 N NaOH (pH 11.8) | 15 | 919.8 | 54.8 | 360 |
| 0.05 N NaOH (pH 12.7) | 5 | 1,011 | 55.2 | 340 |
| 0.05 N NaOH (pH 12.7) | 15 | 704.9 | 53.2 | 820 |
| 0.4 N NaOH (pH 13.4) | 5 | 966.7 | 54.8 | 380 |

In another practical application of the above-described methods, immobilized oligonucleotides were used as primers in TMA reactions. As a preliminary step to establish the versatility of the technique, TMA reactions were first conducted using promoter-primers immobilized to solid surfaces through streptavidin-biotin linkages. Those having an ordinary level of skill in the art will appreciate that the TMA technique employs a set of opposed primers—a "promoter-primer" and an "opposite strand" primer. The promoter-primer typically has a T7 phage RNA polymerase promoter sequence appended to the 5'-end of a sequence which is complementary to a target strand that is to be amplified.

The following Example describes the preparation of a device having biotinylated oligonucleotides uniformly immobilized to the wells of a streptavidin-coated multiwell plate, and use of the device for detecting the products of a nucleic acid amplification reaction. Although amplicon production may be assessed by a single measurement at the conclusion of an amplification reaction (i.e., "endpoint" detection), the procedures described below monitored amplicon synthesis in the reaction as a function of time (i.e., "real-time" detection) at constant temperature. Amplicons were detected during the reaction by a method employing a soluble molecular beacon hybridization probe that yielded a fluorescent emission only upon hybridizing the target amplicon.

Example 7 illustrates how target nucleic acids were detected using a TMA reaction that employed an amplification primer immobilized to a solid surface by streptavidin-biotin interaction. In this instance an HIV-specific promoter-primer was immobilized.

EXAMPLE 7

Nucleic Acid Amplification Using an Immobilized Primer

A streptavidin-coated plastic 96-well plate (Labsystems/ThermoLabsystems) was used for conducting parallel TMA reactions using either an immobilized promoter-primer in combination with a soluble opposite strand primer, or a pair of soluble primers in a solution TMA control reaction. An HIV-specific promoter-primer that included a biotin moiety (Glen Research) joined through two 18 atom glycol linkers (Glen Research) to the 5'-end of the sequence AATTTAATAC-GACTCACTATAGGGAGAGTTTGTAT-GTCTGTTGCTATTAT (SEQ ID NO:3) was first dissolved in a binding buffer that included 10 mM Tris (pH 8.0), 0.1 mM EDTA and 100 mM NaCl. This biotinylated promoter-primer was then immobilized by contacting the wells of the plate for 60 minutes at room temperature (23° C.) with 100 µl aliquots of a solution that contained either 10 pmol or 100 pmol of the oligonucleotide. To remove any residual promoter-primers that were not immobilized, wells of the plate were washed three times with 100 µl of binding buffer, and once with a primeness amplification reagent that included deoxyribonucleotides, ribonucleotides and co-factors in a Tris-buffered solution, all at room temperature. The details of reagent compositions that may be used for conducting TMA reactions have been given by Kacian et al., in U.S. Pat. No. 5,480,784, the disclosure of this patent being incorporated by reference herein. According to the manufacturer's specifications, the streptavidin-coated plate used in this procedure had a biotin binding density of about 20 pmoles per well. No attempt was made to determine the amount or density of primers that actually bound to the plate. Each well received an aliquot containing 20 pmoles of the opposite strand primer having the sequence ACAGCAGTACAAATGGCAG (SEQ ID NO:4). The number of copies of HIV target polynucleotide included in reactions conducted in the presence of the immobilized promoter-primer ranged from $10^2$-$10^3$ in a preliminary experiment, and from $10^4$-$10^6$ in a repeat procedure. Negative control reactions omitted the HIV target polynucleotide. Solution TMA was performed using either 0.1, 1 or 10 pmoles of a non-biotinylated soluble promoter-primer otherwise having the same nucleotide sequence as the immobilized oligonucleotide, and either 0, $10^2$, $3\times10^2$ or $10^3$ copies of the HIV target. Mixtures were covered with 75 µl of inert oil to prevent evaporation, and amplification primers were hybridized to target nucleic acids by heating to 60° C. for 10 minutes. Each reaction also included approximately 18 pmoles of an amplicon-specific molecular beacon having a fluorescein moiety at its 5'-end, a DABCYL quencher moiety at its 3'-end, and a nucleotide sequence given by GCGAGUACAGUG-CAGGGCUCGC (SEQ ID NO:5). Amplification reactions were initiated by adding an enzyme reagent that included Moloney Murine Leukemia Virus (MMLV) reverse transcriptase and T7 RNA polymerase, also in accordance with U.S. Pat. No. 5,480,784 which has been incorporated by reference hereinabove, and then incubating the plate at 42° C. The appearance of fluorescent signals in the wells was monitored as a function of time for 70 minutes using a FLUOROSKAN ASCENT (Labsystems/ThermoLabsystems) microplate fluorometer.

Results from these procedures showed that target nucleic acids could be detected in amplification reactions that employed immobilized primers, although with a level of sensitivity that was reduced somewhat when compared with solution-based reactions that employed only soluble primers. All negative control reactions gave only baseline signals, thereby confirming that no amplification had taken place in the absence of target nucleic acids. Solution TMA reactions gave easily detectable fluorescent signals above baseline over the range of all target amounts that were tested. Fluorescent signals increased in a time-dependent manner in amplification reactions that employed the immobilized primer when at least $10^4$ copies of the target were present. In aggregate, these results demonstrated that immobilized primers could be used for detecting target polynucleotides using TMA reactions, and that amplicon production was sufficiently high to permit monitoring as a function of time in the isothermal reaction.

To illustrate the generality of a system for conducting nucleic acid amplification reactions using surface-immobilized primers, and to further demonstrate the utility of the invented coupling chemistry, TMA reactions were next conducted using primers covalently immobilized to plastic and glass surfaces. As in the preceding Example, the promoter-primer was immobilized to the solid surface and the opposite strand primer was free in solution. Possible advantages of the covalent immobilization scheme over streptavidin-biotin immobilization include extended shelf-life of the device, and the need for less stringent storage conditions.

Example 8 illustrates how the above-described covalent coupling chemistry was used to create a device useful for conducting nucleic acid amplification reactions. Although the procedure particularly describes amplification reactions conducted using primers immobilized through amide bonds to plastic surfaces, or through amide or other bonds to glass surfaces, the success obtained in these procedures indicates that alternative immobilization chemistries would be successful, and so are embraced by the present invention.

EXAMPLE 8

Nucleic Acid Amplification Using Primers Covalently Coupled to Plastic and Glass Surfaces An HIV-specific promoter-primer containing a reactive amine group joined through two 18 atom glycol linkers to the sequence of SEQ ID NO:3 was covalently coupled to the inner surface of a polystyrene 96-well plate essentially as described in Example 5. In this procedure the entire bottom surface of each well was contacted with a solution containing the amplification primer that was to be immobilized. Parallel sets of wells were coupled to the oligonucleotide using either 25 or 250 pmoles of the promoter-primer and the above-described EDAC activation chemistry in MOPS buffer at pH 6.8. Residual promoter-primer that did not couple to the surface was removed by extensive washing, also as described above. Although no attempt was made to determine the efficiency of primer coupling, previous work using a similar attachment chemistry indicated the binding capacity of the wells had an upper practical limit of about $8\times10^4$ copies $\mu m^{-2}$ (or about $2.4\times10^{12}$ copies/well) and a theoretical maximum of about $10^6$ copies $\mu m^{-2}$ (based on the number of functional groups in the wells as reported by the manufacturer). The plate was stored desiccated until being used for conducting TMA reactions. Amplification reactions were carried out using about 20 pmoles of the opposite strand primer in each well, and about 10 pmoles of the soluble promoter-primer in wells that did not harbor immobilized promoter-primers. Wells containing only soluble primers received 100 copies of the HIV target polynucleotide, and served as solution TMA controls. Wells containing the immobilized promoter-primer and the soluble opposite strand primer received HIV target polynucleotide in amounts ranging from $10^2$-$10^7$ copies. An amplicon-specific molecular beacon that included a Cy5 fluorophore at its 3'-end, a DABCYL quencher moiety at its 5'-end, and a base sequence of 2'-methoxy nucleotides given by GCGAGUACAGUGCAGGGGCUCGC (SEQ ID NO:6) was included in each reaction at a level of about 30 pmoles. As in the previous Example, each well additionally contained deoxyribonucleotides, ribonucleotides and co-factors in a Tris-buffered solution. Amplification reactions were initiated by the addition of an aliquot of enzyme reagent, also as described above. Amplicon synthesis was monitored by fluorescence detection as a function of time using the microplate fluorometer.

Figure 4A:
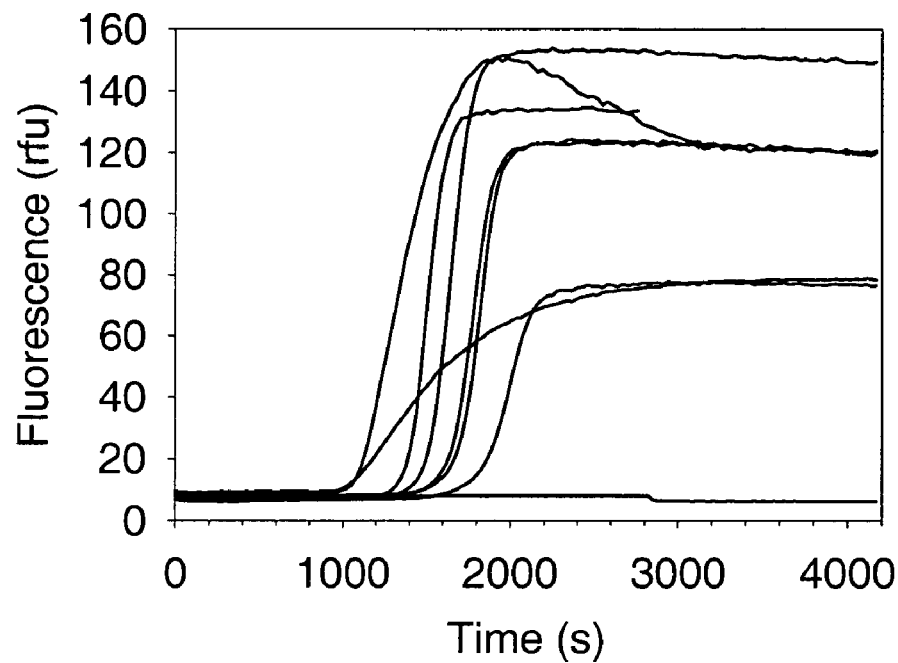
FIGS. 4A-4B are line graphs showing amplicon synthesis (measured by fluorescence) as a function of time for different types of nucleic acid amplification reaction conducted in the presence of soluble molecular beacon hybridization probes.
Figure 4B:
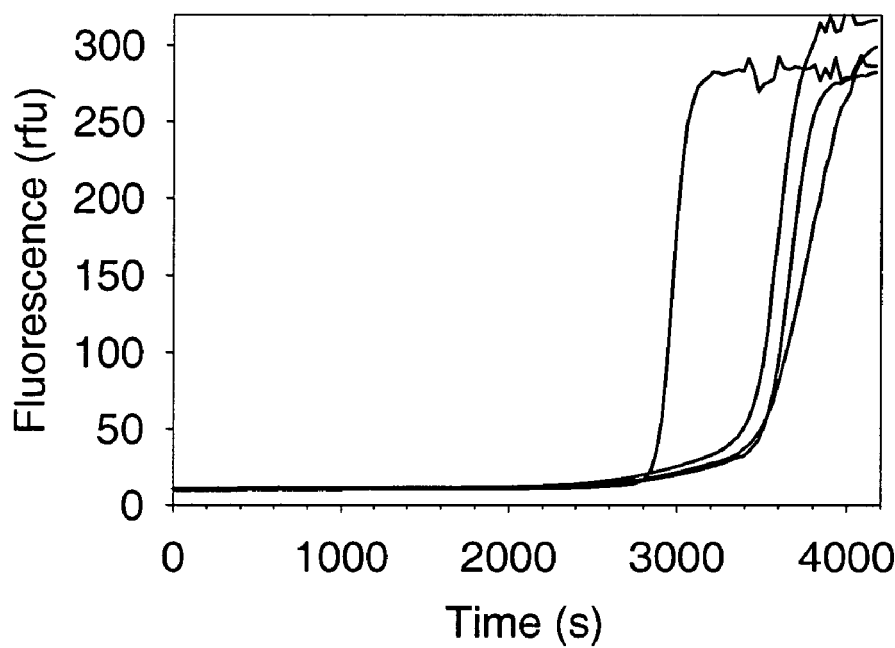

Results from these procedures indicated that amplicons produced in wells having surface-bound promoter-primers could be detected by the end of the reaction period when the level of target input per reaction was as low as 1,000 copies, and perhaps even as low as 100 copies. This level of detectability was advantageously lower than the level achieved in the previous Example. Additionally, fluorescent signals representing the appearance of amplicons in the wells were easily detectable as a function of time within the reaction period when the amount of target in the reaction was 1,000 copies or greater. All control reactions conducted in the absence of added target gave substantially flat time-dependent fluorescent signals. FIG. 4A illustrates the results obtained for a collection of solution TMA replicate trials conducted using 100 copies of the HIV target. Each of the curves shown on the graph represents the time-dependent appearance of the fluorescent signal in different wells of the test plate. FIG. 4B shows results from replicate trials wherein 25 pmoles of promoter-primers were used in the covalent coupling reaction, and wherein the resulting construct was used for performing nucleic acid amplification reactions employing 100,000 copies of the HIV target. The results shown in both panels of the figure indicated that the procedures were characterized by a certain amount of well-to-well variation, but that the results obtained for the two types of amplification reaction formed clusters. For example, most of the solution TMA reactions gave fluorescent signals that emerged above background about 1,000 to 1,500 seconds after initiation of the reactions. Conversely, most of the reactions conducted using immobilized primers gave fluorescent signals that emerged above background about 3,000 seconds after initiation of the reactions. When compared with the time-dependent appearance of the fluorescent signal in solution TMA control trials, reactions conducted using the immobilized promoter-primer exhibited a time delay between the initiation of the reaction and the time at which the fluorescent signal exceeded the background level. This is referred to herein as a delayed "time of emergence" above background. Finally, in contrast with the results obtained in the previous Example, amplicon yields decreased and emergence times increased when larger amounts of promoter-primer were used in the immobilization reactions.

In a related experiment, oligonucleotides were covalently coupled to a glass surface and then used as immobilized primers in TMA reactions. Parallel sets of wells in a glass-bottomed polystyrene 96-well plate were chemically modified essentially by the method of Example 2 to display either functional amine groups (i.e., by reaction with GAPS) or functional sulfhydryl groups (i.e., by reaction with 3MPS). An HIV-specific promoter-primer having the sequence given above, but having a 5' carboxy moiety instead of an amine moiety, was covalently coupled to the inner glass surface of the plate. The carboxylate-terminal primer was then coupled to the derivatized glass surfaces through amide linkages (in the case of the GAPS-treated surface) or through other linkages (in the case of the 3MPS-treated surface) using EDAC-based activation chemistry in a MOPS (pH 6.8) buffer and a two hour reaction time at room temperature, also as described herein. This was accomplished using 25 pmol/100 µl of the 5'-carboxylated promoter-primer for each well. After extensive washing to remove unreacted primer, the plate was used for conducting TMA reactions that were monitored as a function of time. Again, no attempt was made to determine the amount of primers actually coupled to these surfaces. Reactions were conducted using the same opposite strand primer in the amount specified above, and amounts of target that ranged from $10^2$-$10^7$ copies per reaction. Control reactions using soluble primer pairs were carried out in parallel. All reactions included about 30 pmoles of the above-described amplicon-specific Cy5/DABCYL-labeled molecular beacon. Amplification reactions were conducted and monitored as described above.

Results from the procedures conducted using glass-immobilized primers indicated that target nucleic acids were detectable when amplification reactions contained as few as 10,000 copies of target using the amide-linked promoter-primers, and as few as 1,000 copies of target, possibly as few as 100 copies of target, using promoter-primers immobilized by reaction of carboxylated oligonucleotides with a surface displaying sulfhydryl moieties. When compared with control reactions conducted using only soluble primers, the trials conducted using the immobilized primers exhibited a delayed time of emergence above background fluorescence signals. Additionally, the reaction kinetics appeared somewhat slower in trials employing immobilized primers, since the rate of increase in the fluorescent signals was slower than observed in the solution TMA control. In aggregate, these results further illustrated how isothermal nucleic acid amplification reactions can be conducted using immobilized primers, and how amplicon production can be monitored as a function of time.

Having demonstrated that target nucleic acids could be detected by amplification at constant temperature in the presence of soluble molecular beacon hybridization probes, that such amplification could employ immobilized primers, and that amplicon synthesis in the reactions could be monitored in real-time, we next demonstrated that this amplification system could be combined with immobilized molecular beacons to result in a "composite array" of immobilized probes and primers. Two different HIV-specific molecular beacons were used for this purpose. Molecular beacon "L" had an amine-terminal linker in the loop region of the molecule. Molecular beacon "SL" had an amine-terminal linker at the stem-loop junction of the molecule. Both probes were independently coupled as spots in 6×6 arrays inside the wells of a 96-well polystyrene plate using the above-described EDAC activation chemistry.

Signals produced by the molecular beacons in the procedure were assessed by comparing "quenching ratios." As used herein, a quenching ratio is a corrected signal-to-noise ratio that is calculated by first subtracting the signal measured for a buffer control from the signal measured for a sample that included a molecular beacon and a target polynucleotide, and then dividing that result by the value obtained by subtracting the signal measured for a buffer control from the signal measured for a sample containing the molecular beacon but no target or amplification product.

Example 9 describes methods that were used for making and using composite arrays of immobilized primers and molecular beacon hybridization probes. The device incorporating the composite array was used for amplifying and detecting target nucleic acids in a process that can be performed as a closed system.

EXAMPLE 9

Composite Arrays for Amplifying and Detecting Target Nucleic Acids

Polystyrene 96-well plates of the type described in Example 5 were arrayed with spots that independently contained one of two different molecular beacons. The "L" molecular beacon was labeled at the 5'-end with fluorescein, labeled at the 3'-end with DABCYL, and contained a 5 atom internucleotide linker between nucleotide positions 13 and 14 of the sequence CCGAGGGUACAGUGCAGGGCUCGG (SEQ ID NO:7). From this internucleotide linker, two 18 atom glycol moieties were attached, terminating with n-hexylamine. The oligonucleotide was synthesized using 2'-methoxy nucleotide analogs. The loop portion of this molecular beacon L contained a chemical linker that was useful for immobilization to a solid surface. The "SL" molecular beacon was similarly labeled at the 5'-end with fluorescein, labeled at the 3'-end with DABCYL, and contained a 5 atom internucleotide linker between nucleotide positions 17 and 18 of the sequence of SEQ ID NO:5. From this internucleotide linker, two 18 atom glycol moieties were attached, terminating with n-hexylamine. This oligonucleotide was also synthesized using 2'-methoxy nucleotide analogs. The chemical linker used for immobilizing molecular beacon SL to a solid surface was positioned at the stem-loop junction of the molecule. The molecular beacons were immobilized as separately arrayed spots using a BIOCHIP ARRAYER from Packard Bioscience Co. (Meriden, Conn.). Each spot in the array represented delivery of approximately 3 fmoles of a single probe species. Coupling reactions were carried out by spotting the molecular beacons in a solution of 0.1 M MOPS buffer (pH 6.8), 0.1 M EDAC, and 1% PEG at room temperature, and then incubating the spotted plate in a humid chamber in the dark. After 48 hours, solutions were removed and wells were soaked in 0.4 M NaOH, 0.1 mM EDTA and 0.2% TWEEN-20 for 15 minutes. Wells were manually washed six times with 1× TEN buffer (50 mM Tris (pH 8.0), 0.1 mM EDTA, and 50 mM NaCl) at room temperature, washed six times with water using an automated plate washer, and then vacuum desiccated for at least 12 hours. The wells of arrayed plates prepared according to these procedures were either used directly for conducting amplification reactions employing soluble primers, or further coupled with promoter-primers containing reactive amine groups essentially as described in Example 8. In this procedure the arrayed surface was completely contacted with a solution containing the amplification primer that was to be immobilized. This was done by pipetting the primer-containing solution into the well containing the array, thereby immersing the array so that primers immobilized uniformly over the available plastic surface of well. Plates constructed by this latter method comprised an array of immobilized molecular beacons interspersed among a field of immobilized primers to produce a structure which is referred to herein as a "composite array." In this Example both the hybridization probe and the oligonucleotide primer were linked to the plastic surface of the multiwell plate by covalent amide bonds.

To demonstrate that the arrayed molecular beacon probes were useful for detecting target nucleic acid amplification products, wells containing the immobilized probes were used for conducting TMA reactions using either immobilized primers or soluble primers (i.e., solution TMA). Amplification reactions conducted using the arrayed molecular beacons were carried out using $10^5$ copies of the HIV target. A parallel set of control reactions using immobilized or soluble primers included above-described soluble amplicon-specific Cy5/DABCYL-labeled molecular beacon, and either $10^5$ or $10^2$ copies of the HIV target, respectively. A negative control omitted the HIV target. Variables used in this procedure are summarized in Table 5. Amplification reactions were prepared and initiated as described above, and then monitored using the microplate fluorometer for the time-dependent appearance of fluorescent signals indicating amplicon synthesis. This procedure was used to verify the integrity of all reagents used in the procedure. At the conclusion of a 70 minute reaction time, the plate was transferred to a TYPHOON 8600 imager (Molecular Dynamics; Piscataway, N.J.) and scanned using appropriate excitation and emission wavelengths to quantify fluorescent signals emitted from each spot in the array. Conditions used for the scanning included: an excitation wavelength of 532 nm, an emission wavelength of 526 nm, PMT voltage set to 700 volts, 50 μm resolution, and mean fluorescence intensities measured from $3.5 \times 10^4$ μm² areas. Scanning was repeated following a "heat/cool" step in which the plate was first incubated at 60° C. for 60 minutes, and then cooled at room temperature for 80 minutes.

TABLE 5

Variables for Testing Arrayed Molecular Beacons

| promoter-primer | opposite sense primer | Molecular Beacon | HIV Target Amount (copies) |
| --- | --- | --- | --- |
| soluble | soluble | array | $10^5$ |
| immobilized | soluble | array | $10^5$ |
| immobilized | soluble | soluble | $10^5$ |
| soluble | soluble | soluble | $10^2$ |

Figure 5A:
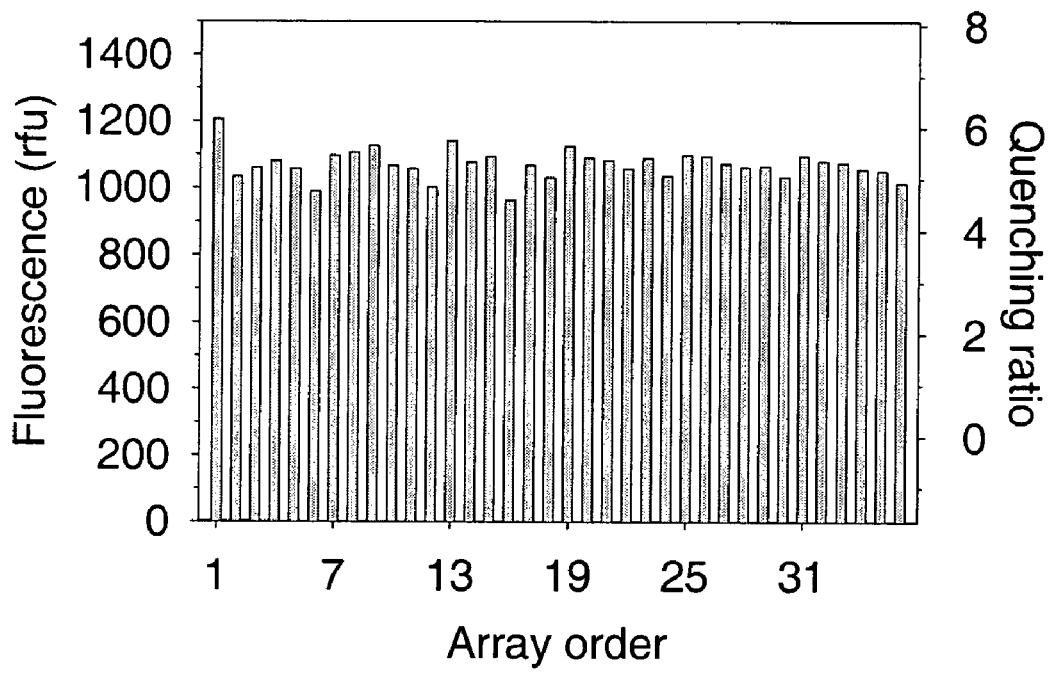
FIGS. 5A-5D are a series of bar graphs showing fluorescence results for immobilized molecular beacon hybridization probes.
Figure 5B:
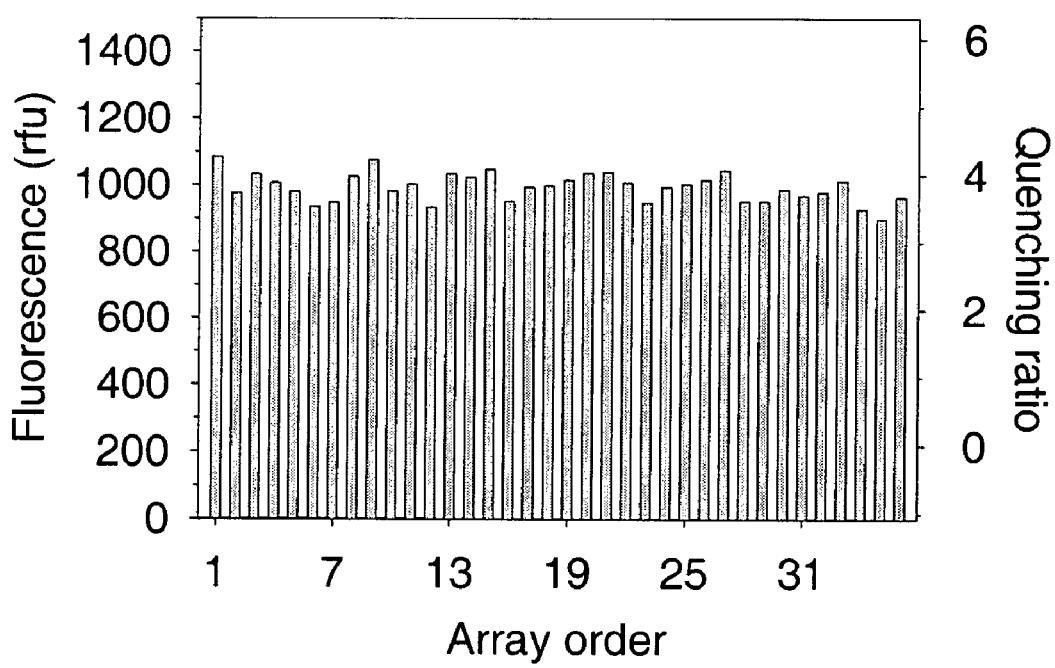
Figure 5C:
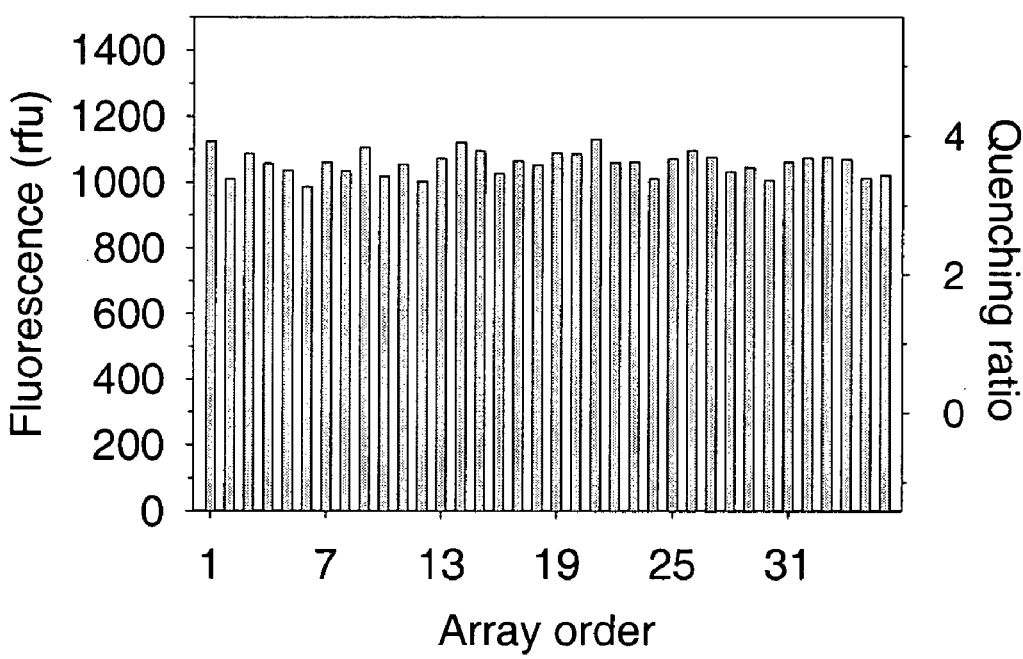
Figure 5D:
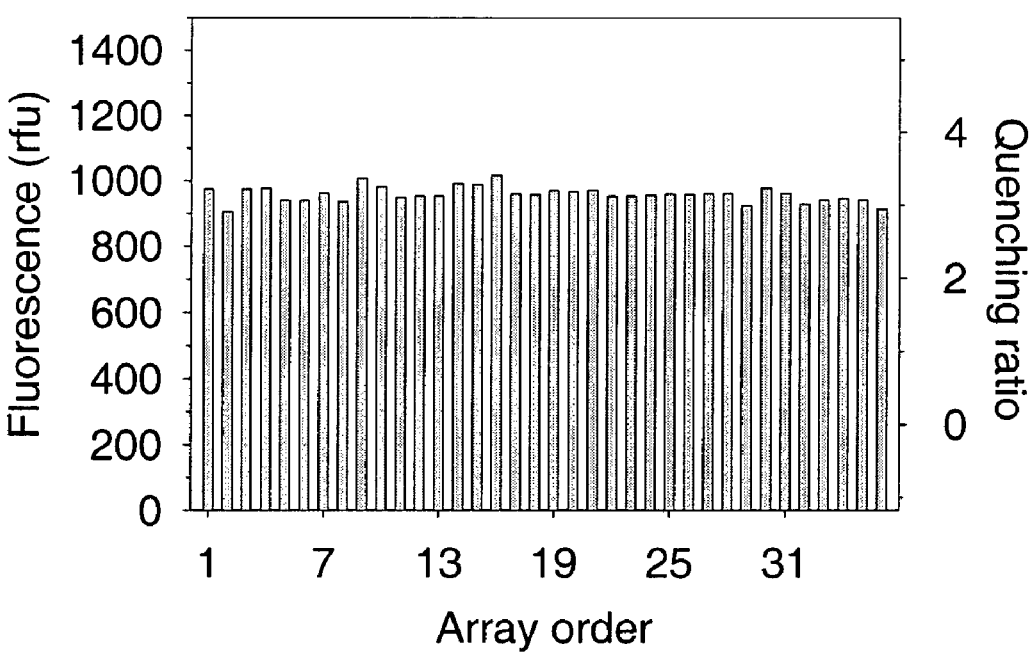

Results from these procedures indicated that the molecular beacon arrays advantageously yielded increased fluorescent signals following amplification of the target nucleic acid using either soluble only, or a combination of soluble and immobilized primers. Control reactions conducted using soluble primers and soluble molecular beacons gave signals that increased as a function of time in 7 out of 8 wells, thereby indicating that all reagents performed as expected. Similarly, time-dependent increases in fluorescence were observed in 6 out of 8 wells containing immobilized promoter-primers and soluble molecular beacons, essentially confirming the results obtained in the previous Example. FIGS. 5A-B show the results of fluorescence measurements from each of 36 spots in a 6×6 array of molecular beacons contained in a representative well in which a TMA reaction employing only soluble primers had been conducted. Panels A and B show results for molecular beacons L and SL, respectively. Each spot in one of the arrays corresponded to an independently arrayed sample of the identical molecular beacon. As will be apparent from reviewing the graphs, the quenching ratio for each of the spots was about 5 for molecular beacon L and about 3.5-4 for molecular beacon SL, with only minimal variation among the signals representing different spots within each array. Thus, the results shown in FIGS. 5A-B indicated that immobilized molecular beacons could be used for detecting amplicons in nucleic acid amplification reactions that were conducted using soluble primers. FIGS. 5C-D show the results of fluorescence measurements from each spot in 6×6 arrays of molecular beacons contained in representative wells in which TMA reactions employing one immobilized primer and one soluble primer had been conducted. Panels C and D show results for molecular beacons L and SL, respectively. The quenching ratios for each of the spots in the array was about 3.5-4 for molecular beacon L and about 3 for molecular beacon SL, with only minimal variation among the signals representing the different spots. This indicated that a composite array of molecular beacons interspersed among a field of immobilized primers was useful for amplifying and detecting target nucleic acids. Although the results shown in this series of graphs represent measurements taken prior to the heat/cool step, substantially similar results were obtained before and after the heat/cool step.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A device for amplifying and detecting a target nucleic acid, comprising:

a solid support bead having a surface;

an amplification primer immobilized to the surface of said solid support bead, said amplification primer comprising a promoter sequence for an RNA polymerase and a sequence complementary to a first strand of said target nucleic acid; and a labeled hybridization probe separate from the amplification primer immobilized to said surface, wherein said labeled hybridization probe comprises 2'-methoxy nucleotide analogs and a sequence complementary to an amplicon synthesized using said amplification primer and said target nucleic acid as a template in a nucleic acid amplification reaction, and wherein prior to contact of said device with any nucleotide polymerizing enzyme said labeled hybridization probe comprises a detectable label and is immobilized to said surface.

2. The device of claim 1, wherein said surface comprises a material selected from the group consisting of glass and plastic.

3. The device of claim 2, wherein said amplification primer immobilized to said surface is covalently immobilized to the surface of said solid support bead.

4. The device of claim 2, wherein said labeled hybridization probe immobilized to said surface is covalently immobilized to the surface of said solid support bead.

5. The device of claim 2, wherein said amplification primer and said labeled hybridization probe are each covalently immobilized to the surface of said solid support bead.

6. The device of claim 1, wherein said labeled hybridization probe comprises a fluorephore moiety and a quencher moiety.

7. The device of claim 1, wherein said device comprises two labeled hybridization probes immobilized to said surface, and wherein said two labeled hybridization probes comprise different sequences.

8. The device of claim 7, wherein prior to contact of said device with any nucleotide polymerizing enzyme there is immobilized to the surface of said solid support bead only one amplification primer sequence having a 3'-end that can be extended by a DNA polymerase using as a template said first strand of the target nucleic acid or the complement thereof.

9. The device of claim 1, wherein prior to contact of said device with any nucleotide polymerizing enzyme there is immobilized to the surface of said solid support bead only one amplification primer sequence having a 3'-end that can be extended by a DNA polymerase using as a template said first strand of the target nucleic acid or the complement thereof.

10. The device of claim 1, wherein said device is in contact with a solution comprising an RNA amplification product that is not immobilized to said device.

* * * * *